United States Patent
Yamakawa et al.

(10) Patent No.: US 8,268,997 B2
(45) Date of Patent: Sep. 18, 2012

(54) PHENYL-SUBSTITUTED 1,3,5-TRIAZINE COMPOUND, PROCESS FOR PRODUCING THE SAME, AND ORGANIC ELECTROLUMINESCENT DEVICE CONTAINING THE SAME AS COMPONENT

(75) Inventors: Tetsu Yamakawa, Tokyo (JP); Hidenori Aihara, Kanagawa (JP); Naoko Yanai, Tokyo (JP); Tsuyoshi Tanaka, Kanagawa (JP); Yoko Honma, Kanagawa (JP); Masaru Sato, Kanagawa (JP)

(73) Assignees: Tosoh Corporation, Yamaguchi (JP); Sagami Chemical Research Institute, Kanagawa (JP)

( * ) Notice: Subject to any disclaimer, the term of this patent is extended or adjusted under 35 U.S.C. 154(b) by 233 days.

(21) Appl. No.: 12/595,795

(22) PCT Filed: Mar. 14, 2008

(86) PCT No.: PCT/JP2008/054756
§ 371 (c)(1),
(2), (4) Date: Oct. 13, 2009

(87) PCT Pub. No.: WO2008/129912
PCT Pub. Date: Oct. 30, 2008

(65) Prior Publication Data
US 2010/0249406 A1    Sep. 30, 2010

(30) Foreign Application Priority Data
Apr. 12, 2007 (JP) .................. 2007-104808

(51) Int. Cl.
C07D 401/10 (2006.01)
C07D 401/14 (2006.01)
C07D 403/14 (2006.01)
C09K 11/06 (2006.01)
C07B 61/00 (2006.01)
H01L 51/50 (2006.01)
(52) U.S. Cl. ...................... 544/180; 313/504
(58) Field of Classification Search ............ 544/180; 313/504
See application file for complete search history.

(56) References Cited

U.S. PATENT DOCUMENTS
6,225,467 B1    5/2001    Esteghamatian et al.
6,352,791 B1    3/2002    Fink et al.
7,994,316 B2 *  8/2011    Yamakawa et al. .......... 544/180

FOREIGN PATENT DOCUMENTS
| | | |
|---|---|---|
| EP | 1930329 | 8/2006 |
| JP | 6-136359 | 5/1994 |
| JP | 6-207169 | 7/1994 |
| JP | 2003-045662 | 2/2003 |
| JP | 2003-282270 | 10/2003 |
| JP | 2004/022334 | 1/2004 |
| JP | 2005-104986 | 4/2005 |
| JP | 2006-199677 | 8/2006 |
| JP | 2007-137829 | 6/2007 |
| JP | 2007/314503 | 12/2007 |
| WO | 95/25097 | 9/1995 |
| WO | 2004-080975 | 9/2004 |
| WO | 2007/023840 | 3/2007 |

OTHER PUBLICATIONS
International Search Report issued with respect to PCT/JP2008/054756, mailed May 13, 2008.

* cited by examiner

*Primary Examiner* — Venkataraman Balasubramanian
(74) *Attorney, Agent, or Firm* — Greenblum & Bernstein, P.L.C.

(57) ABSTRACT

A phenyl-substituted 1,3,5-triazine compound represented by the general formula (1);

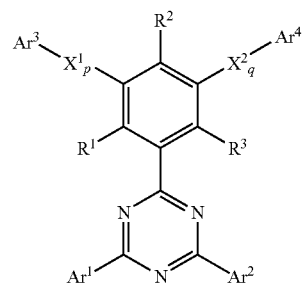

(1)

wherein $Ar^1$ and $Ar^2$ independently represent substituted or unsubstituted phenyl, naphthyl or biphenylyl group; $R^1$, $R^2$ and $R^3$ independently represent hydrogen atom or methyl group; $X^1$ and $X^2$ independently represent substituted or unsubstituted phenylene, naphthylene or pyridylene group; p and q independently represent an integer of 0 to 2; and $Ar^3$ and $Ar^4$ independently represent substituted or unsubstituted pyridyl or phenyl group. This compound is suitable for an organic electroluminescent device.

12 Claims, 1 Drawing Sheet

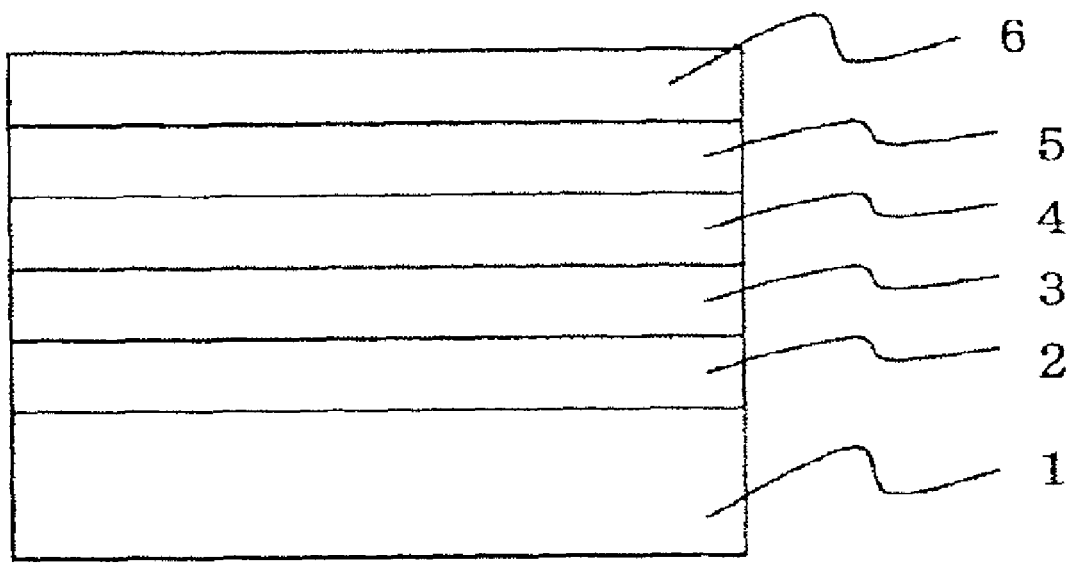

PHENYL-SUBSTITUTED 1,3,5-TRIAZINE COMPOUND, PROCESS FOR PRODUCING THE SAME, AND ORGANIC ELECTROLUMINESCENT DEVICE CONTAINING THE SAME AS COMPONENT

TECHNICAL FIELD

This invention relates to a phenyl-substituted 1,3,5-triazine compound and a process for producing the compound. More particularly it relates a phenyl-substituted 1,3,5-triazine compound useful for an organic electroluminescent device, and, an organic electroluminescent device having at least one organic compound layer comprising the phenyl-substituted 1,3,5-triazine compound, which exhibits a reduced power consumption.

BACKGROUND ART

An organic electroluminescent device has a multilayer structure comprising (i) a luminescent layer comprising a light emitting compound, (ii) a hole transport layer and an electron transport layer, which sandwich the luminescence layer, and (iii) an anode and a cathode, which sandwich the hole transport layer, the luminescent layer and the electron transport layer. The organic electroluminescent device utilizes light emission (fluorescence or phosphorescence) occurring at deactivation of an exciton formed by the binding of electron with hole, which are injected in the luminescence layer.

In recent years, a wide spread attention is attracted to an organic electroluminescent device for next-generation flat panel displays. This is because, first, an electroluminescent device can be made into a thin film and be rendered light in weight; secondly, power consumption is small due to the spontaneous light emission; and thirdly, the device structure is simple and thus the production cost is low. Various methods can be adopted for the production thereof, which include, for example, vacuum deposition, spin coating, ink-jet printing, off-set printing and thermal transfer printing.

Now various mobile devices such as cell phones, mobile music devices, and personal digital assistant (PDA) are widely used. However, if mobile devices can be larger in size or more precise, organic electroluminescent devices are expected to be used in, for example, flat panel displays, lighting systems with a surface-light-emitting source, flexible paper-like displays, wearable displays and transparent see-through displays. Its use is expected to be rapidly spread.

However, an organic electroluminescent device still has many technical problems to be solved. Especially its driving voltage is high and the efficiency is low, and thus, its power consumption is large.

The above-mentioned technical problems arise due to the property of the material of organic electroluminescent device, especially the property of electron transport material. Many materials including triarylamine derivatives have been proposed as a hole transport material, but, only several reports are found as to the electron transport material. Tris(8-quinolinolato)-aluminum (III) (Alq) is already put in practical use as an electron transport material, but, its property is poor as compared with a hole transport material such as, for example, N,N'-bis(1-naphthyl)-N,N'-diphenyl-4,4'-biphenyl (NPD), and an organic electroluminescent material comprising the electron transport material has also poor property.

As other electron transport materials, there can be mentioned oxadiazole derivatives (patent document 1), quinoxaline derivatives (patent document 2), triazole derivatives (patent document 3), silacyclopentadiene derivatives (patent document 4), quinoline derivatives (patent document 5), benzimidazole derivatives (patent document 6) and benzothiazole derivatives (non-patent document 1). However, organic electroluminescent devices comprising these electron transport materials still have problems in that their driving voltage is high, the film are readily crystallized, and their service life is short.

Recently, 1,3,5-triazine compounds have been proposed as other electron transport materials (patent documents 7, 8, 9, 10 and 11).

Patent document 1: JP-A H6-136359
Patent document 2: JP-A H6-207169
Patent document 3: WO95/25097
Patent document 4: JP-A 2005-104986
Patent document 5: JP-A 2006-199677
Patent document 6: WO2004/080975
Patent document 7: JP-A 2003-045662
Patent document 8: JP-A 2003-282270
Patent document 9: JP-A 2004-022334
Patent document 10: U.S. Pat. No. 6,225,467
Patent document 11: U.S. Pat. No. 6,352,791
Non-patent document 1: Applied Physics Letters, vol. 89, 063504, 2006

DISCLOSURE OF THE INVENTION

Problems to Be Solved by the Invention

Organic electroluminescent devices comprising the heretofore proposed 1,3,5-triazine compounds still do not exhibit a sufficiently reduced driving voltage and are insufficient in efficiency.

Means for Solving the Problems

The inventors made an extensive research to solve the above-mentioned problems, and found that the specific phenyl-substituted 1,3,5-triazine compound according to the present invention is capable of being made into an amorphous thin film by any of vacuum deposition method and spin coating method, and, organic electroluminescent devices comprising the phenyl-substituted 1,3,5-triazine compound as electron transport material exhibit a sufficiently reduced driving voltage and a high efficiency, a long service life, and a minimized increase in voltage. On the basis of these findings, the present invention has been completed.

Thus, in one aspect of the present invention, there is provided a phenyl-substituted 1,3,5-triazine compound characterized by being represented by the following general formula (1):

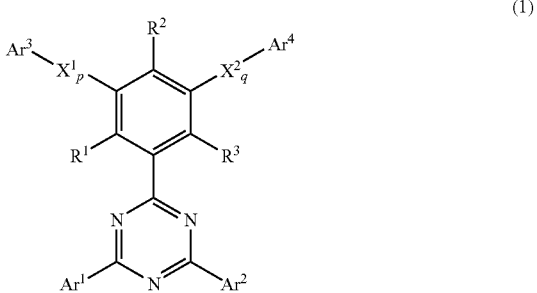

(1)

wherein:

Ar¹ and Ar² each independently represent a phenyl group, a naphthyl group or a biphenylyl group, wherein these groups may have at least one substituent selected from an alkyl group having 1 to 6 carbon atoms and a trifluoromethyl group;

R¹, R² and R³ each independently represent a hydrogen atom or a methyl group;

X¹ and X² each independently represent a phenylene group, a naphthylene group or a pyridylene group, wherein these groups may have at least one substituent selected from an alkyl group having 1 to 4 carbon atoms and a fluorine atom;

p and q each independently represent an integer in the range of 0 to 2, wherein, when p is 2, the adjacent X¹s may be the same or different, and when q is 2, the adjacent X²s may be the same or different; and Ar³ and Ar⁴ each independently represent a pyridyl group which may have at least one substituent selected from an alkyl group having 1 to 4 carbon atoms and a fluorine atom, or a phenyl group which may have at least one substituent selected from an alkyl group having 1 to 4 carbon atoms and a fluorine atom.

In another aspect of the present invention, there is provided a process for producing a phenyl-substituted 1,3,5-triazine compound represented by the following general formula (1a):

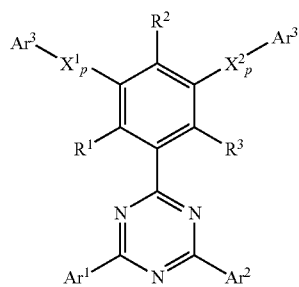

(1a)

wherein Ar¹, Ar², R¹, R², R³, X¹, p and Ar³ are the same as defined below with regard to the general formulae (2a) and (3), characterized by coupling a compound represented by the following general formula (2a) with a compound represented by the following general formula (3) in the presence of a metal catalyst;

(2a)

wherein X¹, p and Ar³ are the same as defined above with regard to the general formulae (1), and M represents a —ZnR⁴ a group, a —MgR⁵ group, a —SnR⁶R⁷R⁸ group, a —B(OH)₂ group, a —BR⁹ group, a —BF₃⁻(Z¹)⁺ group or a —SiR¹⁰R¹¹R¹² group, wherein R⁴ and R⁵ represent a chlorine atom, a bromine atom or an iodine atom; R⁶, R⁷ and R⁸ each independently represent an alkyl group having 1 to 4 carbon atoms; R⁹ represents a methoxy group, an isopropoxy group, a 2,3-dimethylbutane-2,3-dioxy group, an ethylenedioxy group, a 1,3-propanedioxy group or a 1,2-phenylenedioxy group; (Z¹)⁺ represents an alkali metal ion or a quaternary ammonium ion; and R¹⁰, R¹¹ and R¹² each independently represent a methyl group, an ethyl group, a methoxy group, an ethoxy group or a chlorine atom;

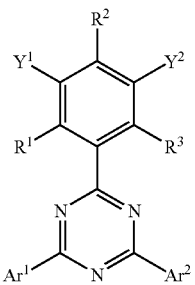

(3)

wherein
Ar¹, Ar², R¹, R² and R³ are the same as defined above with regard to the general formula (1), and Y¹ and Y² each independently represent a chorine atom, a bromine atom, an iodine atom or a trifluoromethylsulfonyloxy group.

In a further aspect of the present invention, there is provided a process for producing a phenyl-substituted 1,3,5-triazine compound represented by the above-mentioned general formula (1), characterized by coupling a compound represented by the above-mentioned general formula (2a) with a compound represented by the above-mentioned general formula (3) in the presence of a metal catalyst to give a compound represented by the following general formula (4); and then, coupling the compound of formula (4) with a compound represented by the following general formula (2b) in the presence of a metal catalyst;

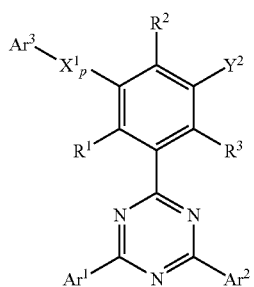

(4)

wherein Ar¹, Ar², R¹, R², R³, p, Ar³ and Y² are the same as defined above with regard to the formulae (2a) and (3);

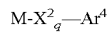

(2b)

wherein
X², q and Ar⁴ are the same as defined above with regard to the general formula (1), and M is the same as defined above with regard to the general formula (2a).

In a further aspect of the present invention, there is provided a process for producing a phenyl-substituted 1,3,5-triazine compound represented by the above-mentioned general formula (1), characterized by coupling a compound represented by the above-mentioned general formula (2b) with a compound represented by the above-mentioned general formula (4) in the presence of a metal catalyst.

In a further aspect of the present invention, there is provided a compound characterized by being represented by the above-mentioned general formula (4).

In a further aspect of the present invention, there is provided a process for producing a compound represented by the above-mentioned general formula (4), characterized by coupling a compound represented by the above-mentioned general formula (2a) with a compound represented by the above-mentioned general formula (3) in the presence of a metal catalyst.

In a further aspect of the present invention, there is provided an organic electroluminescent device characterized by containing as a component a phenyl-substituted 1,3,5-triazine compound represented by the above-mentioned general formula (1).

Effect of the Invention

The phenyl-substituted 1,3,5-triazine compound according to the present invention gives a thin film having outstanding properties in surface smoothness, amorphousness, heat resistance, electron transportability, hole blocking capability, resistance to oxidation and reduction, moisture resistance, oxygen resistance and electron injection property.

BRIEF DESCRIPTION OF THE DRAWINGS

FIG. 1 illustrates a schematic cross-section of an organic electroluminescent device made in Example 12.

EXPLANATION OF REFERENCE NUMERALS

1. Glass substrate with transparent ITO electrode
2. Hole injection layer
3. Hole transport layer
4. Light emitting layer
5. Electron transport layer
6. Cathode layer

BEST MODE FOR CARRYING OUT THE INVENTION

The invention will now be described in detail.

$Ar^1$ and $Ar^2$ each independently represent a phenyl group, a naphthyl group or a biphenylyl group, wherein these groups may have at least one substituent selected from an alkyl group having 1 to 6 carbon atoms and a trifluoromethyl group;

As specific examples of the phenyl group which may have at least one substituent selected from an alkyl group having 1 to 6 carbon atoms and a trifluoromethyl group, there can be mentioned groups of phenyl, p-tolyl, m-tolyl, o-tolyl, p-trifluoromethylphenyl, m-trifluoromethylphenyl, o-trifluoromethylphenyl, 2,4-dimethylphenyl, 3,5-dimethylphenyl, mesityl, 2-ethylphenyl, 3-ethylphenyl, 4-ethylphenyl, 2,4-diethylphenyl, 3,5-diethylphenyl, 2-propylphenyl, 3-propylphenyl, 4-propylphenyl, 2,4-dipropylphenyl, 3,5-dipropylphenyl, 2-isopropylphenyl, 3-isopropylphenyl, 4-isopropylphenyl, 2,4-diisopropylphenyl and 3,5-diisopropylphenyl.

The above-mentioned phenyl group further includes, for example, groups of 2-butylphenyl, 3-butylphenyl, 4-butylphenyl, 2,4-dibutyllphenyl, 3,5-dibutylphenyl, 2-tert-butylphenyl, 3-tert-butylphenyl, 4-tert-butylphenyl, 2,4-di-tert-butylphenyl, 3,5-di-tert-butylphenyl, 2-pentylphenyl, 3-pentylphenyl, 4-pentylphenyl, 2,4-dipentylphenyl, 3,5-dipentylphenyl, 2-neopentylphenyl, 3-neopentylphenyl, 4-neopentylphenyl, 2,4-dineopentylphenyl, 3,5-dineopentylphenyl, 2-hexylphenyl, 3-hexylphenyl, 4-hexylphenyl, 2,4-dihexylphenyl, 3,5-dihexylphenyl, 2-cyclohexylphenyl, 3-cyclohexylphenyl, 4-cyclohexylphenyl, 2,4-dicyclohexylphenyl and 3,5-dicyclohexylphenyl.

In view of the outstanding property of an organic electroluminescent device, groups of phenyl, p-tolyl, m-tolyl, 4-ethylphenyl, 4-propylphenyl, 4-isopropylphenyl, 4-butylphenyl, 4-tert-butylphenyl, 4-pentylphenyl, 4-hexylphenyl, 3,5-dimethylphenyl and 4-cyclohexylphenyl are preferable. Groups of phenyl, p-tolyl, m-tolyl, 3,5-dimethylphenyl, 4-butylphenyl and 4-tert-butylphenyl are especially preferable.

As specific examples of the biphenylyl group which may have at least one substituent selected from an alkyl group having 1 to 6 carbon atoms and a trifluoromethyl group, there can be mentioned groups of 4-biphenylyl, 4'-methylbiphenyl-4-yl, 4'-trifluoromethylbiphenyl-4-yl, 2,5-dimethylbiphenyl-4-yl, 2',5'-dimethylbiphenyl-4-yl, 4'-ethylbiphenyl-4-yl, 4'-propylbiphenyl-4-yl, 4'-butylbiphenyl-4-yl, 4'-tert-butylbiphenyl-4-yl, 4'-hexylbiphenyl-4-yl, 3-biphenylyl, 3'-methylbiphenyl-3-yl, 3'-trifluoromethylbiphenyl-3-yl, 3'-ethylbiphenyl-3-yl, 3'-propylbiphenyl-3-yl, 3'-butylbiphenyl-3-yl, 3'-tert-butylbiphenyl-3-yl and 3'-hexylbiphenyl-3-yl.

In view of the outstanding property of an organic electroluminescent device, groups of 4-biphenylyl, 4'-methylbiphenyl-4-yl, 4'-tert-butylbiphenyl-4-yl, 3-biphenylyl, 3'-methylbiphenyl-3-yl and 3'-tert-butylbiphenyl-3-yl are preferable. 4-Biphenylyl group and 3-biphenylyl group are especially preferable.

As specific examples of the naphthyl group which may have at least one substituent selected from an alkyl group having 1 to 6 carbon atoms and a trifluoromethyl group, there can be mentioned groups of 1-naphthyl, 4-methylnaphthalen-1-yl, 4-trifluoromethylnaphthalen-1-yl, 4-ethylnaphthalen-1-yl, 4-propylnaphthalen-1-yl, 4-butylnaphthalen-1-yl, 4-tert-butylnaphthalen-1-yl, 4-hexylnaphthalen-1-yl, 5-methylnaphthalen-1-yl, 5-trifluoromethylnaphthalen-1-yl, 5-ethylnaphthalen-1-yl, 5-propylnaphthalen-1-yl, 5-butylnaphthalen-1-yl, 5-tert-butylnaphthalen-1-yl, 5-hexylnaphthalen-1-yl, 2-naphthyl, 6-methylnaphthalen-2-yl, 6-trifluoromethylnaphthalen-2-yl, 6-ethylnaphthalen-2-yl, 6-propylnaphthalen-2-yl, 6-butylnaphthalen-2-yl, 6-tert-butylnaphthalen-2-yl, 6-hexylnaphthalen-2-yl, 7-methylnaphthalen-2-yl, 7-trifluoromethylnaphthalen-2-yl, 7-ethylnaphthalen-2-yl, 7-propylnaphthalen-2-yl, 7-butylnaphthalen-2-yl, 7-tert-butylnaphthalen-2-yl and 7-hexylnaphthalen-2-yl.

In view of the outstanding property of an organic electroluminescent device, groups of 1-naphthyl, 4-methylnaphthalen-1-yl, 4-tert-butylnaphthalen-1-yl, 5-methylnaphthalen-1-yl, 5-tert-butylnaphthalen-1-yl, 2-naphthyl, 6-methylnaphthalen-2-yl, 6-tert-butylnaphthalen-2-yl, 7-methylnaphthalen-2-yl and 7-tert-butylnaphthalen-2-yl are preferable. 1-Naphthyl group and 2-naphthyl group are especially preferable.

$R^1$, $R^2$ and $R^3$ each independently represent a hydrogen atom or a methyl group. Of these, a hydrogen atom is preferable in view of the outstanding property of an organic electroluminescent device.

$X^1$ and $X^2$ each independently represent a phenylene group, a naphthylene group or a pyridylene group, wherein these groups may have at least one substituent selected from an alkyl group having 1 to 4 carbon atoms and a fluorine atom.

As specific examples of the phenylene group for $X^1$ and $X^2$, there can be mentioned groups of 1,3-phenylene, 2-methyl-1,3-phenylene, 4-methyl-1,3-phenylene, 5-methyl-1,3-phenylene, 2-tert-butyl-1,3-phenylene, 4-tert-butyl-1,3-phenylene, 5-tert-butyl-1,3-phenylene, 1,4-phenylene, 2-methyl-1,4-phenylene, 2-tert-butyl-1,4-phenylene, 2-fluoro-1,4-phenylene, 3-fluoro-1,4-phenylene, 2,3,5,6-tetrafluoro-1,4-phenylene and 2,5-dimethyl-1,4-phenylene.

As specific examples of the naphthylene group for $X^1$ and $X^2$, there can be mentioned groups of 1,4-naphthylene, 2-methyl-1,4-naphthylene, 5-methyl-1,4-naphthylene, 6-methyl-1,4-naphthylene, 2-tert-butyl-1,4-naphthylene, 5-tert-butyl- 1,4-naphthylene, 6-tert-butyl-1,4-naphthylene, 1,5-naphthylene, 2-methyl-1,5-naphthylene, 3-methyl-1,5-naphthylene, 4-methyl-1,5-naphthylene, 2-tert-butyl-1,5-naphthylene, 3-tert-butyl-1,5-naphthylene, 4-tert-butyl-1,5-naphthylene, 2,6-naphthylene, 1-methyl-2,6-naphthylene, 3-methyl-2,6-naphthylene, 4-methyl-2,6-naphthylene, 1-tert-butyl-2,6-naphthylene, 3-tert-butyl-2,6-naphthylene and 4-tert-butyl-2,6-naphthylene.

As specific examples of the pyridylene group for $X^1$ and $X^2$, there cab be mentioned groups of 2,4-pyridylene, 3-methyl-2,4-pyridylene, 5-methyl-2,4-pyridylene, 6-methyl-2,4-pyridylene, 3-tert-butyl-2,4-pyridylene, 5-tert-butyl-2,4-pyridylene, 6-tert-butyl-2,4-pyridylene, 2,5-pyridylene, 3-methyl-2,5-pyridylene, 4-methyl-2,5-pyridylene, 6-methyl-2,5-pyridylene, 3-tert-butyl-2,5-pyridylene, 4-tert-butyl-2,5-pyridylene, 6-tert-butyl-2,5-pyridylene, 2,6-pyridylene, 3-methyl-2,6-pyridylene, 4-methyl-2,6-pyridylene, 3-tert-butyl-2,6-pyridylene and 4-tert-butyl-2,6-pyridylene.

The pyridylene group for $X^1$ and $X^2$ further includes, for example, 3,5-pyridylene, 2-methyl-3,5-pyridylene, 4-methyl-3,5-pyridylene, 6-methyl-3,5-pyridylene, 2-tert-butyl-3,5-pyridylene, 4-tert-butyl-3,5-pyridylene, 6-tert-butyl-3,5-pyridylene, 3,6-pyridylene, 2-methyl-3,6-pyridylene, 4-methyl-3,6-pyridylene, 5-methyl-3,6-pyridylene, 2-tert-butyl-3,6-pyridylene, 4-tert-butyl-3,6-pyridylene, 5-tert-butyl-3,6-pyridylene, 4,6-pyridylene, 2-methyl-4,6-pyridylene, 3-methyl-4,6-pyridylene, 5-methyl-4,6-pyridylene, 2-tert-butyl-4,6-pyridylene, 3-tert-butyl-4,6-pyridylene and 5-tert-butyl-4,6-pyridylene.

In view of the outstanding property of an organic electroluminescent device, groups of 1,3-phenylene, 1,4-phenylene, 2,3,5,6-tetrafluoro-1,4-phenylene, 2,5-dimethyl-1,4-phenylene, 1,4-naphthylene, 1,5-naphthylene, 2,6-naphthylene, 2,4-pyridylene, 2,6-pyridylene, 3,5-pyridylene 3,6-pyridylene and 4,6-pyridylene are preferable.

$Ar^3$ and $Ar^4$ each independently represent a pyridyl group which may have at least one substituent selected from an alkyl group having 1 to 4 carbon atoms and a fluorine atom, or a phenyl group which may have at least one substituent selected from an alkyl group having 1 to 4 carbon atoms and a fluorine atom.

As specific examples of the pyridyl group for $Ar^3$ and $Ar^4$ which may have at least one substituent selected from an alkyl group having 1 to 4 carbon atoms and a fluorine atom, there can be mentioned groups of 2-pyridyl, 3-methylpyridin-2-yl, 4-methylpyridin-2-yl, 5-methylpyridin-2-yl, 6-methylpyridin-2-yl, 3-ethylpyridin-2-yl, 4-ethylpyridin-2-yl, 5-ethylpyridin-2-yl, 6-ethylpyridin-2-yl, 3-propylpyridin-2-yl, 4-propylpyridin-2-yl, 5-propylpyridin-2-yl, 6-propylpyridin-2-yl, 3-butylpyridin-2-yl, 4-butylpyridin-2-yl, 5-butylpyridin-2-yl, 6-butylpyridin-2-yl, 3-tert-butylpyridin-2-yl, 4-tert-butylpyridin-2-yl and 5-tert-butylpyridin-2-yl.

The pyridyl group for $Ar^3$ and $Ar^4$ further includes, for example, 6-tert-butylpyridin-2-yl, 3-fluoropyridin-2-yl, 4-fluoropyridin-2-yl, 5-fluoropyridin-2-yl, 6-fluoropyridin-2-yl, 3-pyridyl, 2-methylpyridin-3-yl, 4-methylpyridin-3-yl, 5-methylpyridin-3-yl, 6-methylpyridin-3-yl, 2-ethylpyridin-3-yl, 4-ethylpyridin-3-yl, 5-ethylpyridin-3-yl, 6-ethylpyridin-3-yl, 2-propylpyridin-3-yl, 4-propylpyridin-3-yl, 5-propylpyridin-3-yl, 6-propylpyridin-3-yl, 2-butylpyridin-3-yl, 4-butylpyridin-3-yl, 5-butylpyridin-3-yl, 6-butylpyridin-3-yl, 2-tert-butylpyridin-3-yl and 4-tert-butylpyridin-3-yl.

The pyridyl group for $Ar^3$ and $Ar^4$ further includes, for example, 5-tert-butylpyridin-3-yl, 6-tert-butylpyridin-3-yl, 2-fluoropyridin-3-yl, 2-fluoropyridin-4-yl, 2-fluoropyridin-5-yl, 2-fluoropyridin-6-yl, 4-pyridyl, 2-methylpyridin-4-yl, 3-methylpyridin-4-yl, 2-ethylpyridin-4-yl, 3-ethylpyridin-4-yl, 2-propylpyridin-4-yl, 3-propylpyridin-4-yl, 2-butylpyridin-4-yl, 3-butylpyridin-4-yl, 2-tert-butylpyridin-4-yl, 3-tert-butylpyridin-4-yl and 1-fluoropyridin-4-yl.

As specific examples of the phenyl group for $Ar^3$ and $Ar^4$ which may have at least one substituent selected from an alkyl group having 1 to 4 carbon atoms and a fluorine atom, there can be mentioned groups of phenyl, o-tolyl, m-tolyl, p-tolyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-tert-butylphenyl, 3-tert-butylphenyl, 4-tert-butylphenyl, 2-fluorophenyl, 3-fluorophenyl and 4-fluorophenyl.

In view of the outstanding property of an organic electroluminescent device, the pyridyl and phenyl groups for $Ar^3$ and $Ar^4$ are preferably selected from groups of 2-pyridyl, 3-pyridyl, 4-pyridyl, phenyl and 4-tert-butylphenyl.

Further, in view of the outstanding property of an organic electroluminescent device, at least one of $Ar^3$ and $Ar^4$ is more preferably selected from groups of 2-pyridyl, 3-pyridyl and 4-pyridyl. 2-Pyridyl group is especially preferable.

When p is 1 or 2, the $X^1$— and $Ar^3$— containing substituents, i.e., —$X^1$—$Ar^3$ and —$X^1$—$X^1$—$Ar^3$ include, for example, the following skeletal structures (I) through (LXXVI) can be mentioned, but, the substituents —$X^1$—$Ar^3$ and —$X^1$—$X^1$—$Ar^3$ are not particularly limited thereto.

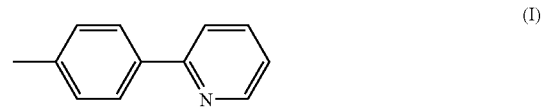

(I)

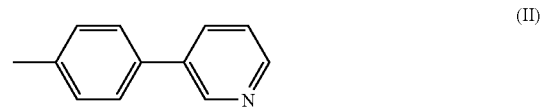

(II)

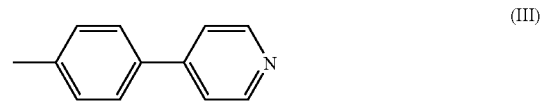

(III)

(IV)

(V)

(VI)

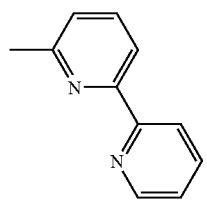
(VII)
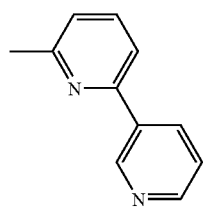
(VIII)
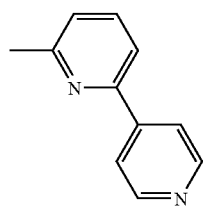
(IX)
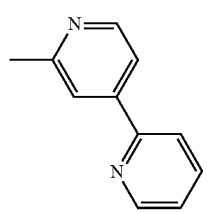
(X)
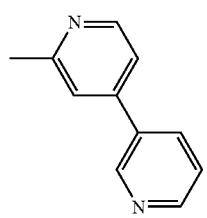
(XI)
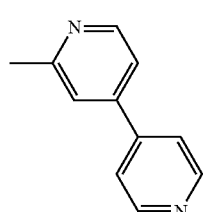
(XII)
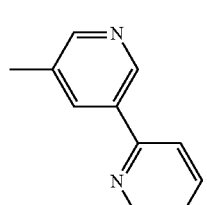
(XIII)
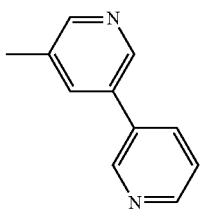
(XIV)
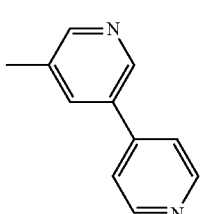
(XV)
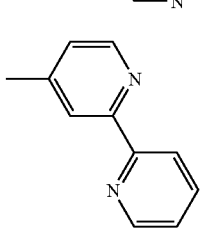
(XVI)
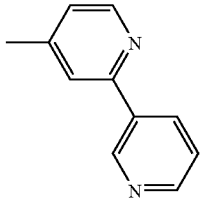
(XVII)
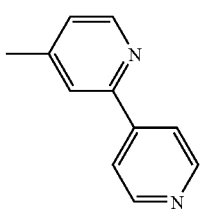
(XVIII)
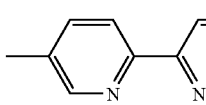
(XIX)
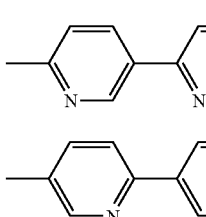
(XX)
(XXI)
(XXII)
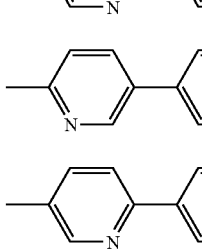
(XXIII)

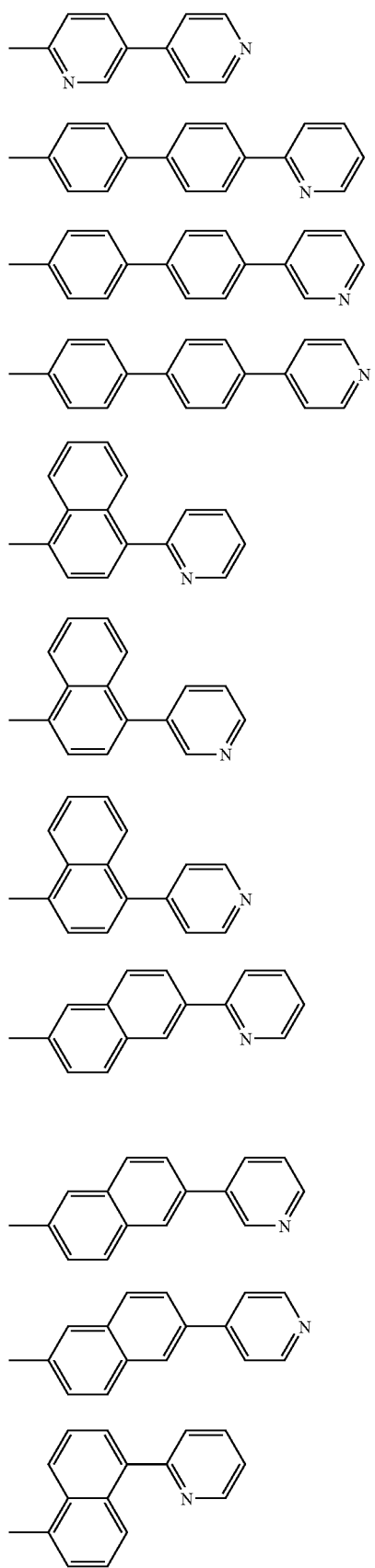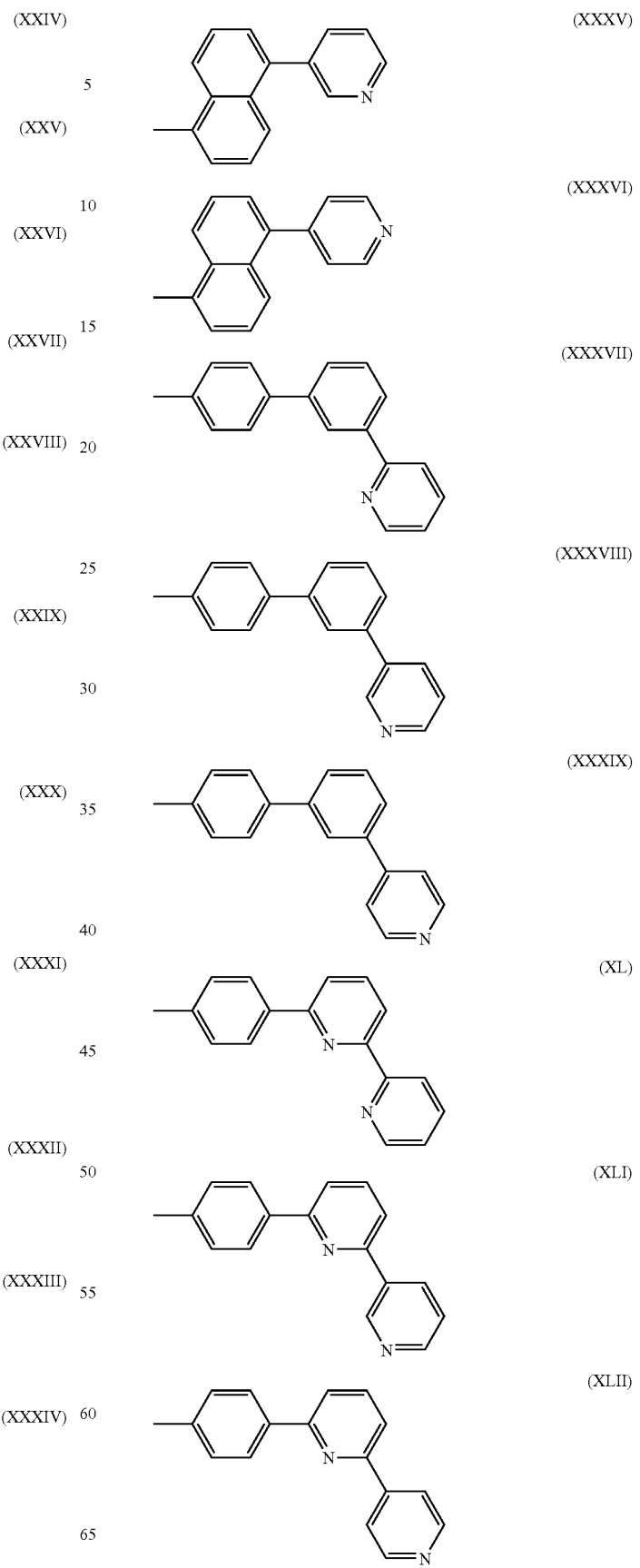

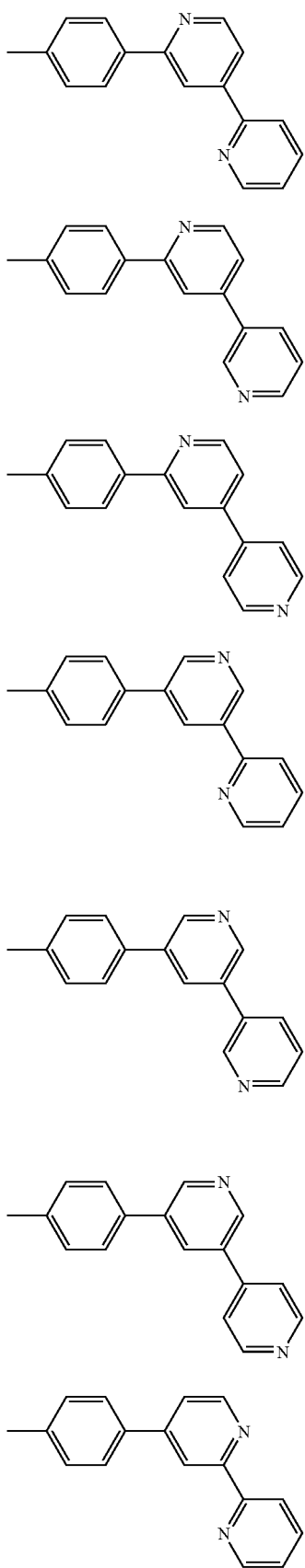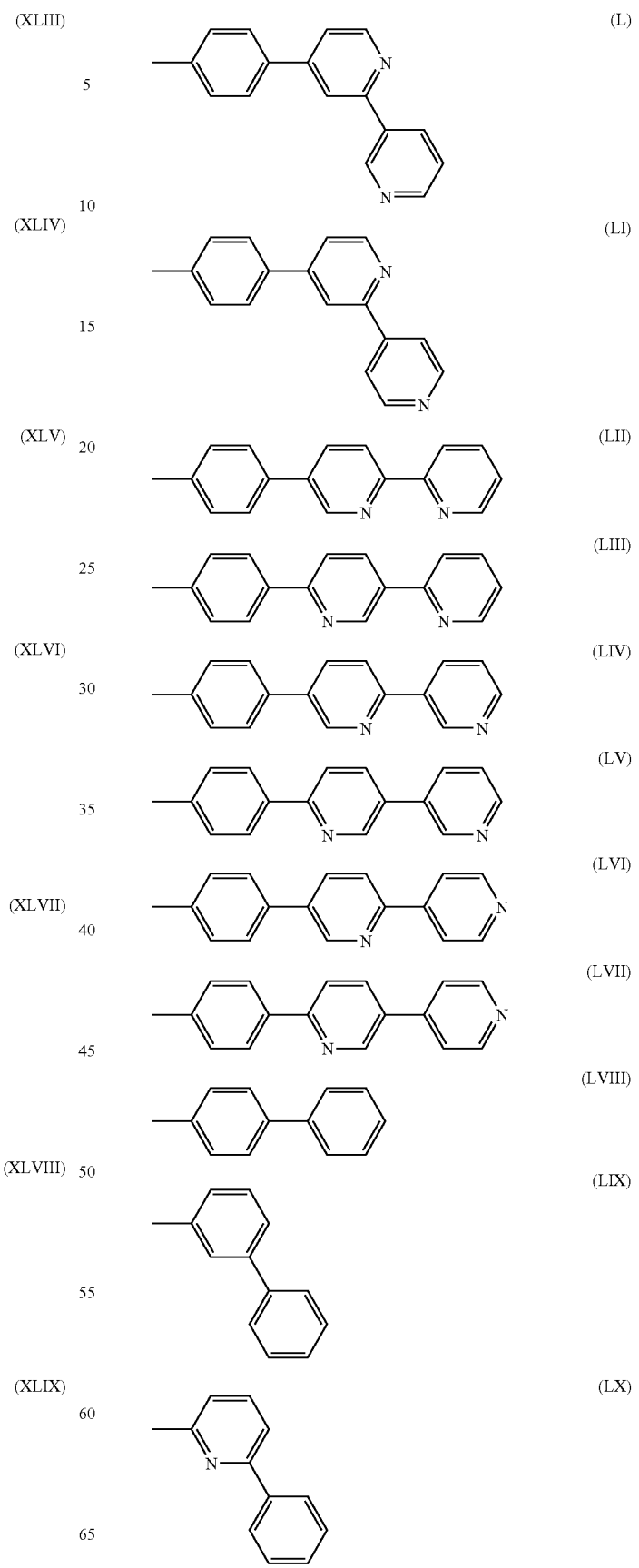

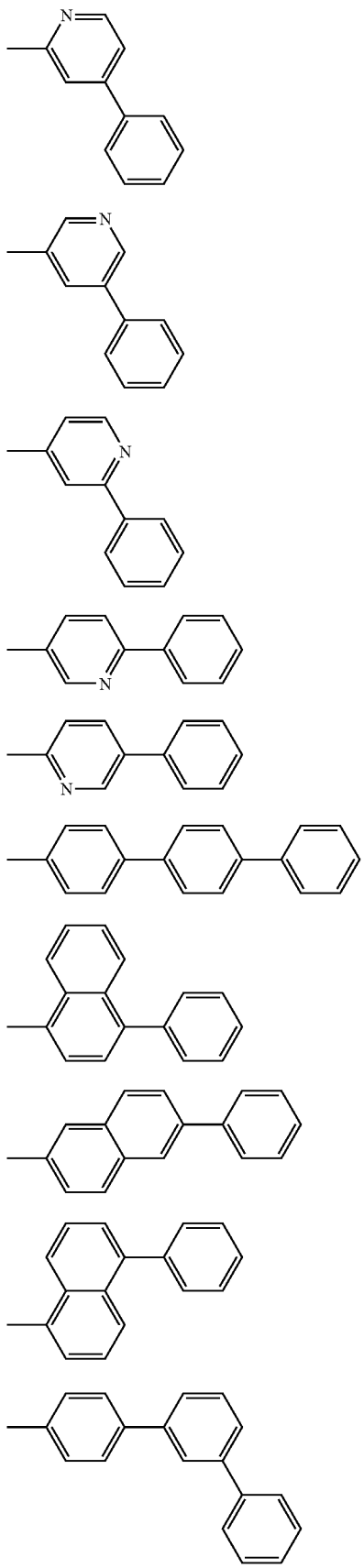
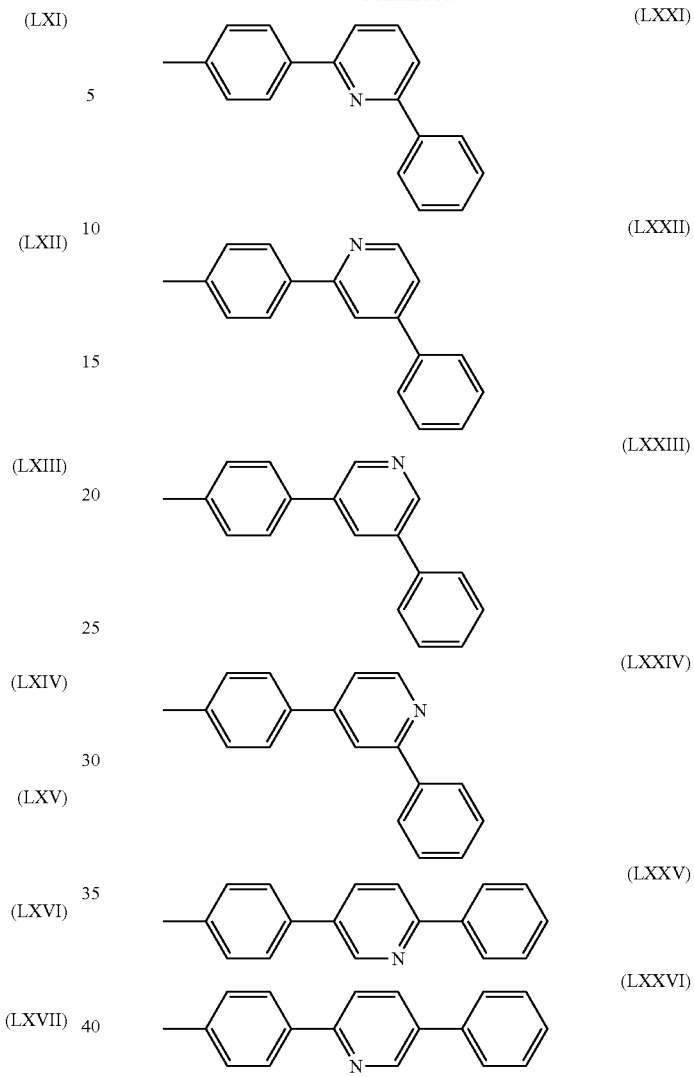

When q is 1 or 2, the $X^2$— and $Ar^4$— containing substituents, i.e., —$X^2$—$Ar^4$ and —$X^2$—$X^2$—$Ar^4$ include, for example, the above-listed skeletal structures (I) through (LXXVI) can be mentioned, but, the substituents —$X^1$—$Ar^3$ and —$X^1$—$X^1$—$Ar^3$ are not particularly limited thereto.

In the general formula (3), $Y^1$ and $Y^2$ are preferably selected from a bromine atom, an iodine atom and a chlorine atom in view of the yield and the selectivity.

The production process according to the present invention will now be described.

Phenyl-substituted 1,3,5-triazine compound (1a) can be produced by a process comprising the following step "P-1" and the succeeding step "A".

Step P-1 comprises the preparation of a compound represented by the above-mentioned general formula (2a), which is used for the preparation of the phenyl-substituted 1,3,5-triazine compound (1a), from a stating compound represented by the following general formula (5a).

(5a)

wherein $X^1$, p, and $Ar^3$ are as defined above, and $Y^3$ represents a leaving group. The reaction in the step P-1 is illustrated by the following scheme.

Step P-1

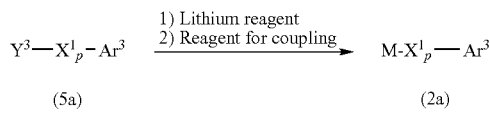

wherein $Y^3$, $X^1$, p, $Ar^3$ and N are the same as defined above.

In step P-1, the compound (5a) is lithiated by a lithium reagent such as butyllithium or tert-butyllithium, and then, the lithiated product is reacted with a reagent for coupling to give the compound (2a) which is conventionally used for a coupling reaction.

As specific examples of the reagent for coupling, there can be mentioned dichloro(tetramethylethylenediamine)zinc(II), zinc chloride, zinc bromide, zinc iodide, trimethyltin chloride, tributyltin chloride, tribuyltin hydride, hexamethyldistannane, hexabutyldistannane, boric acid, trimethyl borate, triisopropyl borate, (2,3-dimethylbutane-2,3-dioxy)borane, (2,3-dimethylbutane-2,3-dioxy)methoxyborane, (2,3-dimethylbutane-2,3-dioxy)isopropoxyborane, ethylenedioxyborane, 1,3-propanedioxyborane, bis(2,3-dimethylbutane-2,3-dioxy)diborane, 1,2-phenylenedioxyborane, trimethoxysilane, triethoxysilane and dichlorodiethylsilane.

By the reaction of the lithiated product with these reagents for coupling, the compound (2a) can be obtained, which includes, for example, the following species as M: —ZnCl, —ZnBr, —ZnI, —Sn(CH$_3$)$_2$, —Sn(C$_4$H$_9$)$_3$, —B(OH)$_2$, —B(OMe)$_2$, —B(O-iso-C$_3$H$_7$)$_2$, —B(2,3-dimethylbutane-2, 3-dioxy), —B(ethylenedioxy), —B(1,3-propanedioxy), —B(1,2-phenylenedioxy), —Si(OCH$_3$)$_3$, —Si(OC$_2$H$_5$)$_3$ and —SiCl$_2$ (C$_2$H$_5$).

As a modification of the above-mentioned step, when the lithiated product is reacted with a boric acid ester as a reagent for coupling, its reaction product can be reacted with hydrofluoric acid, and then the thus-obtained reaction product is treated with, for example, potassium carbonate, cesium carbonate or tetrabutylammonium fluoride to give a compound having a salt species as M such as —BF$_3^-$K$^+$, —BF$_3^-$Cs$^+$ or —BF$_3^-$N(C$_4$H$_9$)$_4^+$.

Alternatively, the compound (5a) can be directly reacted with, for example, magnesium bromide or isopropylmagnesium bromide, without lithiation of the compound (5a), to give a compound (2a) having a species as M such as —MgBr.

The obtained compound (2a) can be isolated for use as a raw material for the production of the phenyl-substituted 1,3,5-triazine compound (1a). Alternatively, the compound (2a) can be directly, i.e., without isolation, used for the production of the compound (1a).

In step P-1, the lithiated product is preferably reacted with a reagent for coupling selected from dichloro-(tetramethylethylenediamine)zinc(II), zinc chloride, zinc bromide, zinc iodide, trimethyltin chloride, tributyltin chloride and boric acid, to give a compound (2a) having a species as M selected from —ZnCl, —ZnBr, —ZnI, —Sn(CH$_3$)$_3$, —Sn(C$_4$H$_9$)$_3$ and —B(OH)$_2$.

The leaving group $Y^3$ includes, for example, a chlorine atom, a bromine atom, an iodine atom and a trifluoromethylsulfonyloxy group. Of these, a bromine atom and an iodine atom are preferable because the yield is high.

In the step P-1, the molar ratio of a lithium reagent to the compound (5a) is preferably in the range of 1:1 to 5:1, and especially preferably 1:1 to 3:1 in view of high yield.

In the step P-1, the reactions of the compound (5a) with the lithium reagent and suceedingly with the reagent for coupling is carried out in a reaction medium. The reaction medium includes, for example, tetrahydrofuran, toluene, benzene, diethyl ether, xylene, chloroform and dichloromethane. These reaction mediums may be used either alone or in combination. Preferably tetrahydrofuran is used alone in view of high yield.

The concentration of the compound (5a) in the step P-1 is preferably in the range of 10 mmol/L to 10,000 mmol/L, and more preferably 50 mmol/L to 200 mmol/L in view of high yield.

In the step P-1, the lithiation reaction is preferably carried out at a temperature in the range of −150° C. to −20° C., and more preferably −100° C. to −60° C. The reaction time is preferably in the range of 1 minute to 3 hours, and more preferably 15 minutes to 1 hour in view of high yield.

In the step P-1, the molar ratio of a reagent for coupling to the compound (5a) is preferably in the range of 1:1 to 1:10, and especially preferably 1:1.5 to 1:3 in view of high yield.

In the step P-1, after the addition of a reagent for coupling, the reaction is preferably carried out in temperature ranges including a low temperature region of −150° C. to −20° C. and a succeeding high temperature region of −20° C. to 50° C. More preferably the reaction is carried out in temperature ranges including a low temperature region of −100° C. to −60° C. and a succeeding elevated high temperature region of 0° C. to 30° C. in view of high yield.

In the step P-1, the reaction time after the addition of the reagent for coupling varies depending the conditions such as the particular substrate and the reaction scale, and is not particularly limited. Preferably the reaction in the low temperature region is carried out in the range of 1 minute to 1 hour, and more preferably 5 minutes to 30 minutes in view of high yield. Preferably the reaction in the high temperature region is carried out in the range of 10 minutes to 10 hours, and more preferably 30 minutes to 5 hours in view of high yield.

The compound (5a) can be prepared by a coupling reaction of, for example, $Y^3$—$X^1$—$Y^3$, $Y^3$—$X^1$—$X^1$—$Y^3$, $Y^3$—$Ar^3$, $Y^3$—$X^1$—$Ar^3$, $Y^3$—$X^1$-M, $Y^3$—$X^1$—$X^1$-M, M-$AR^3$ or M-$X^1$—$Ar^3$, using a general metal catalyst according to the method described in, for example, Tsuji: "Palladium Reagents and Catalysts", John Wiley & Sons, 2004.

The step A following the above-mentioned step P-1 will be described. In the step A, the compound (2a) is reacted with the compound (3) in the presence of a metal catalyst to give the phenyl-substituted 1,3,5-triazine compound according to the present invention. The reaction in the step A is illustrated by the following scheme.

Step A

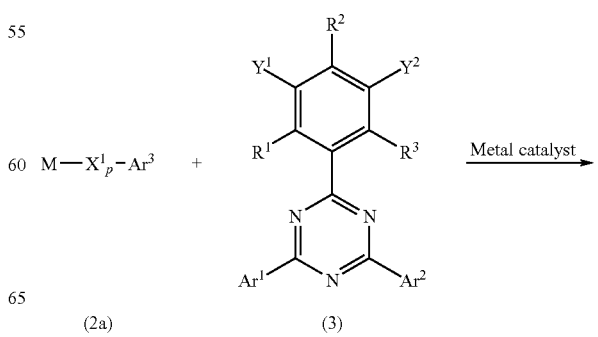

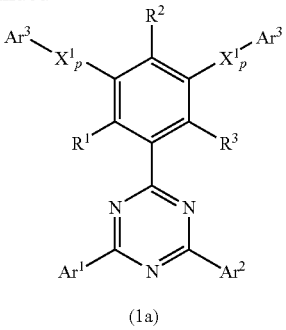

(1a)

wherein M, $X^1$, p, $Ar^3$, $Ar^1$, $Ar^2$, $R^1$, $R^2$, $R^3$, $Y^1$ and $Y^2$ are the same as defined above.

The metal catalyst which can be used in the step A is described in, for example, Metal-catalyzed Cross-coupling Reactions, Wiley-VCH, 1998; Modern Organonickel Chemistry, Wiley-VCR, 2005; and Journal of the American Chemical Society, vol. 126, p 3686-3687, 2004. Such metal catalysts include, for example, a palladium catalyst, a nickel catalyst, an iron catalyst, a ruthenium catalyst, a platinum catalyst, a rhodium catalyst, an iridium catalyst, an osmium catalyst and a cobalt catalyst.

Of these, a palladium catalyst, a nickel catalyst and an iron catalyst are preferable because the yield is high. A palladium catalyst is especially preferable.

As specific examples of the palladium catalyst, there can be mentioned palladium metal such as palladium black or palladium sponge; supported palladium metals such as palladium/alumina, palladium/carbon, palladium/silica, palladium/Y-type zeolite, palladium/A-type zeolite, palladium/X-type zeolite, palladium/mordenite and palladium/ZSM-5; and palladium metal salts such as palladium chloride, palladium bromide, palladium iodide, palladium acetate, palladium trifluoroacetate, palladium nitrate, palladium oxide, palladium sulfate, palladium cyanide, sodium hexachloropalladate, potassium hexachloropalladate, sodium tetrachloropalladate, potassium tetrachloropalladate, potassium tetrabromopalladate, ammonium tetrachloropalladate and ammonium hexachloropalladate.

The palladium catalyst further includes complex compounds such as, for example, π-allylpalladium chloride dimmer, palladium acetylacetonate, tetra(acetonitrile)palladium borofluoride, dichlorobis(acetonitrile)palladium, dichlorobis(benzonitrile)-palladium, bis(dibenzylideneacetone)palladium, tris(dibenzylideneacetone)dipalladium, dichlorodiammine-palladium, tetraamminepalladium nitrate, tetraamminepalladium tetrachloropalladate, dichlorodipyridinepalladium, dichloro(2,2'-bipyridyl)palladium, dichloro(phenanthroline)-palladium, (tetramethylphenanthroline)palladium nitrate, diphenanthrolinepalladium nitrate, bis(tetramethylphenanthroline)palladium nitrate, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium and dichloro[1,1'-bis(diphenylphosphino)ferrocene]palladium.

The palladium catalyst may be used either alone or in combination with a tertiary phosphine.

As specific examples of the tertiary phosphine used, there can be mentioned triphenylphosphine, trimethylphosphine, triethylphosphine, tripropylphosphine, triisopropylphosphine, tributylphosphine, triisobutylphosphine, tri(tert-butyl)-phosphine, trineopentylphosphine, tricyclohexylphosphine, trioctylphosphine, tri(hydroxymethyl)phosphine, tris(2-hydroxyethyl)phosphine, tris(3-hydroxypropyl) phosphine, tris(2-cyanoethyl)phosphine, (+)-1,2-bis[(2R,5R)-2,5-diethylphosphorano]ethane, triallylphosphine, triamylphophine, cyclohexyldiphenylphosphine, methyldiphenylphosphine and ethyldiphenylphosphine.

The tertiary phosphine further includes, for example, propyldiphenylphosphine, isopropyldiphenylphosphine, butyldiphenylphosphine, isobutyldiphenylphosphine, tert-butyldiphenylphosphine, 9,9-dimethyl-4,5-bis(diphenylphosphino)xanthene, 2-(diphenylphosphino)-2'-(N,N-dimethylamino)biphenyl, (R)-(+)2-(diphenylphosphino)-2'-methoxy-1,1'-binaphthyl, (−)-1,2-bis[(2R,5R)-2,5-dimethylphosphorano]benzene, (+)-1,2-bis[(2S,5S)-2,5-dimethylphosphino]benzene, (−)-1,2-bis[(2R,5R)-2,5-diethylphosphorano]benzene, (+)-1,2-bis[(2S,5S)-2,5-diethylphosphino]benzene and 1,1'-bis(diisopropylphosphino)ferrocene.

The tertiary phosphine further includes, for example, (−)-1,1'-bis[(2S,4S)-2,4-diethylphosphorano]ferrocene, (R)-(−)-1-[(S)-2-(dicyclohexylphosphino)ferrocenyl]-ethyldicyclohexylphosphne, (+)-1,2-bis[(2R,5R)-2,5-diisopropylphosphorano]benzene, (−)-1,2-bis[(2S,5R)-2,5-diisopropylphosphorano]benzene, (t)-2-(di-tert-butylphosphino)-1,1'-binaphthyl, 2-(di-tert-butylphosphino)-biphenyl, 2-(dicyclohexylphosphino)biphenyl, 2-(dicyclohexyl-phosphino)-2'-methylbiphenyl, bis(diphenylphosphino)methane, 1,2-bis(diphenylphosphino)ethane, 1,2-bis(dipentafluorophenyl-phosphino)ethane and 1,3-bis(diphenylphosphino)propane.

The tertiary phosphine further includes, for example, 1,4-bis(diphenylphosphino)butane, 1,4-bis(diphenylphosphino)-pentane, 1,1'-bis(diphenylphosphino)ferrocene, (2R,3R)-(−)-2,3-bis(diphenylphosphino)-bicyclo[2.2.1]hept-5-en, (2S,3S)-(+)-2,3-bis(diphenylphosphino)-bicyclo[2.2.1]hept-5-en, (2S,3S)-(−)-bis(diphenylphosphino)butane, cis-1,2-bis(diphenylphosphino)ethylene, bis(2-diphenylphosphinoethyl)-phenylphosphine, (2S,4S)-(−)-2,4-1,4-bis(diphenylphosphino)-pentane, (2R,4R)-(−)-2,4-1,4-bis(diphenylphosphino)pentane and R-(+)-1,2-bis(diphenylphosphino)propane.

The tertiary phosphine further includes, for example, (2S,3S)-(+)-1,4-bis(diphenylphosphino)-2,3-o-isopropylidene-2,3-butanediol, tri(2-furyl)phosphine, tris(1-naphthyl)-phosphine, tris[3,5-bis(trifluoromethyl)phenyl]phosphine, tris(3-chlorophenyl)phosphine, tris(4-chlorophenyl)phosphine, tris(3,5-dimethylphenyl)phosphine, tris(3-fluorophenyl)-phosphine, tris(4-fluorophenyl)phosphine, tris(2-methoxyphenyl)phosphine, tris(3-methoxyphenyl) phosphine, tris(4-methoxyphenyl)phosphine, tris(2,4,6-trimethoxyphenyl)-phosphine, tris(pentafluorophenyl) phosphine, tris[4-(perfluorohexyl)phenyl]phosphine and tris (2-thienyl)phosphine.

The tertiary phosphine further includes, for example, trimtolyl)phosphine, tri(o-tolyl)phosphine, tri(p-tolyl)-phosphine, tris(4-trifluoromethylphenyl)phosphine, tris(2,5-xylyl)phosphine, tris(3,5-xylyl)phosphine, 1,2-bis(diphenylphosphino)benzene, (R)-(+)-2,2'-bis-(diphenylphosphino)-1,1'-binaphthyl, (S)-(−)-2,2'-bis(diphenylphosphino)-1,1'-binaphthyl, (±)-2,2'-bis-(diphenylphosphino)-1,1'-binaphthyl, 2,2'-bis-(diphenylphosphino)-1,1'-biphenyl, (S)-(+)-4,12-bis-(diphenylphosphino)-[2.2]paracyclophane, (R)-(−)-4,12-bis-(diphenylphosphino)-[2.2]paracyclophane and (R)-(+)-2,2'-bis (di-p-tolylphosphino)-1,1'-binaphthyl.

The tertiary phosphine further includes, for example, (S)-(−)-2,2′-bis(di-p-tolylphosphino)-1,1′-binaphthyl, bis(2-methoxyphenyl)phenylphosphine, 1,2-bis(diphenylphosphino)benzene, (1R,2R)-(+)-N,N′-bis(2′-diphenylphosphinobenzoyl)-1,2-diaminocyclohexane, (1S,2S)-(+)-N,N′-bis(2′-diphenylphosphinobenzoyl)-1,2-diaminocyclohexane, (±)-N,N′-bis(2′-diphenylphosphinobenzoyl)-1,2-diaminocyclohexane, (1S,2S)-(−)-N,N′-bis(2-diphenylphosphino-1-naphthoyl)-1,2-diaminocyclohexane and (1R,2R)-(+)-N,N′-bis(2′-diphenylphosphino-1-naphthoyl)-1,2-diaminocyclohexane.

The tertiary phosphine further includes, for example, (±)-N,N′-bis(2-diphenylphosphino-1-naphthoyl)diaminocyclohexane, tris(diethylamino)phosphine, bis(diphenylphosphino)acetylene, bis(2-diphenylphospinophenyl)ether, (R)-(−)-1-[(S)-2-(dicyclohexylphosphino)ferrocenyl]ethyldiphenylphodphine, (R)-(−)-1-[(S)-2-(diphenylphosphino)ferrocenyl]ethyldi-tert-butylphosphine, dipotassium bis(p-sulfonatophenyl)phenylphosphine, 2-dicyclohexylphosphino-2′-(N,N-diemthylamino)biphenyl, (S)-(−)-1-[2-(diphenylphosphino-1-naphthyl)isoquinoline, 2-dicyclohexylphosphino-2′,4′,6′-triisopropylbiphenyl and tris(trimethylsilyl)phosphine.

A palladium catalyst used in the step A can be any form of the above-mentioned metal, supported metal, metal salt and complex compound, but, the following palladium catalysts are preferably used in view of high yield: palladium chloride, palladium acetate, π-allylpalladium chloride dimmer, bis(dibenzylideneacetone)-palladium, tris(dibenzylideneacetone)dipalladium, dichlorobis(triphenylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium and dichloro[1,1′-bis(diphenylphosphino)ferrocene]palladium, palladium/alumina and palladium/carbon. Of these, tetrakis(triphenylphosphine)palladium is especially preferable.

Any of the tertiary phosphines recited above may be used in combination with the palladium catalyst, but the following tertiary phosphines are preferably used in view of high yield: triphenylphosphine, trimethylphosphine, triethylphosphine, tributylphosphine, tri(tert-butyl)phosphine, tricyclohexylphosphine, trioctylphosphine, 9,9-dimethyl-4,5-bis(diphenylphosphino)xanthene, 2-(di-tert-butylphosphino)-biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1′-bis(diphenylphosphino)ferrocene, (R)-(+)-2,2′-bis(diphenylphosphino)-1,1′-binaphthyl, (S)-(−)-2,2′-bis(diphenylphosphino)-1,1′-binaphthyl, 2-dicyclohexylphosphino-2′,4′,6′-triisopropylbiphenyl and (±)-2,2′-bis(diphenylphosphino)-1,1′-binaphthyl.

Of these, the following tertiary phosphines are especially preferable: triphenylphosphine, trimethylphosphine, tributylphosphine, tri(tert-butyl)phosphine, tricyclohexylphosphine, trioctylphosphine, 2-(di-tert-butylphosphino)biphenyl, 2-(dicyclohexylphosphino)-biphenyl, 1,2-bis(diphenylphosphino)ethane, 1,3-bis(diphenylphosphino)propane, 1,4-bis(diphenylphosphino)butane, 1,1′-bis(diphenylphosphino)ferrocene, (R)-(+)-2,2′-bis(diphenylphosphino)-1,1′-binaphthyl, (S)-(−)-2,2′-bis(diphenylphosphino)-1,1′-binaphthyl, 2-dicyclohexylphosphino-2′,4′,6′-triisopropylbiphenyl and (±)-2,2′-bis(diphenylphosphino)-1,1′-binaphthyl.

The step A can be carried out to a sufficient extent without addition of a base. However, a base can be added to enhance the yield. As the base added, organic and inorganic bases can be mentioned, which include, for example, lithium carbonate, sodium carbonate, sodium hydrogencarbonate, potassium carbonate, cesium carbonate, potassium fluoride, cesium fluoride, sodium hydroxide, potassium hydroxide, potassium phosphate, triethylamine, butylamine, diisopropylamine and ethyldiisopropylamine.

In the step A, the molar ratio of the compound (2a) to the compound (3) is preferably in the range of 10:1 to 2:1, and especially preferably 5:1 to 2:1 in view of high yield.

The molar ratio of the metal catalyst to the compound (3) in the step A is preferably in the range of 0.001:1 to 0.5:1, and especially preferably 0.01:1 to 0.1:1 in view of high yield.

In the step A, the reaction is carried out in a reaction medium. The reaction medium includes, for example, methanol, ethanol, isopropyl alcohol, N,N-dimethylformamide, dioxane, diethyl ether, xylene, toluene, benzene, tetrahydrofuran, acetonitrile, dichloromethane, dimethylsulfoxide, N-methyl-2-pyrrolidone and hexamethylphosphoric triamide. These reaction mediums may be used either alone or in combination. Preferably dioxane, diethyl ether, toluene and tetrahydrofuran are used in view of high yield.

In the case when the compound (2a) produced in the step P-1 is used without isolation for the step A, the reaction medium used in the step P-1 may be used, as it is, in the step A.

The concentration of the compound (3) in the step A is preferably in the range of 5 mmol/L to 1,000 mmol/L, and more preferably 10 mmol/L to 200 mmol/L in view of high yield.

In the step A, the reaction is preferably carried out at a temperature appropriately chosen in the range of 0° C. to the reflux temperature of the reaction medium used, and more preferably at the reflux temperature of the reaction medium in view of high yield.

The reaction time in the step A is preferably in the range of 10 minutes to 48 hours, and more preferably 30 minutes to 24 hours in view of high yield.

The phenyl-substituted 1,3,5-triazine compound (1a) can be collected by removing the reaction medium from the reaction product after completion of the step A. If desired, the reaction product is purified by, for example, recrystallization, column chromatography or sublimation.

The process for producing the phenyl-substituted 1,3,5-triazine compound (1) will now be described.

The phenyl-substituted 1,3,5-triazine compound (1) is produced by conducting the following step "P-2", and, step "B-1" and succeeding step "B-2", following the above-mentioned step "P-1".

Step P-2 comprises the preparation of a compound represented by the above-mentioned general formula (2b), which is used for the preparation of the phenyl-substituted 1,3,5-triazine compound (1), from a starting compound represented by the following general formula (5b).

wherein $X^2$, q and $Ar^4$ are as defined above, and $Y^4$ represents a leaving group. The reaction in the step P-2 is illustrated by the following scheme.

Step P-2

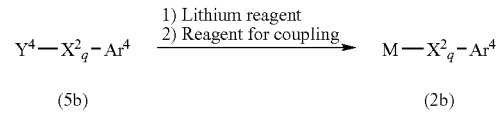

(5b)    (2b)

wherein $Y^4$, $X^2$, q, $Ar^4$ and M are as defined above.

In step P-2, the compound (5b) is lithiated by a lithium reagent such as butyllithium or tert-butyllithium, and then, the lithiated product is reacted with a reagent for coupling to give the compound (2b) which is a species conventionally used for a coupling reaction.

As specific examples of the reagent for coupling, there can be mentioned dichloro(tetramethylethylenediamine)zinc(II), zinc chloride, zinc bromide, zinc iodide, trimethyltin chloride, tributyltin chloride, tribuyltin hydride, hexamethyldistannane, hexabutyldistannane, boric acid, trimethyl borate, triisopropyl borate, (2,3-dimethylbutane-2,3-dioxy)borane, (2,3-dimethyl-butane-2,3-dioxy)methoxyborane, (2,3-dimethylbutane-2,3-dioxy)-isopropoxyborane, ethylenedioxyborane, 1,3-propanedioxyborane, bis(2,3-dimethylbutane-2,3-dioxy)diborane, 1,2-phenylenedioxyborane, trimethoxysilane, triethoxysilane and dichlorodiethylsilane.

By the reaction of the lithiated product with these reagents for coupling, the compound (2b) can be obtained, which includes, for example, the following species as M: —ZnCl, —ZnBr, —ZnI, —Sn(CH$_3$)$_3$, —Sn(C$_4$H$_9$)$_3$, —B(OH)$_2$, —B(OMe)$_2$, —B(O-iso-C$_3$H$_7$)$_2$, —B(2,3-dimethylbutane-2,3-dioxy), —B(ethylenedioxy), —B(1,3-propanedioxy), —B(1,2-phenylenedioxy), —Si(OCH$_3$)$_3$, —Si(OC$_2$H$_5$)$_3$ and —SiCl$_2$(C$_2$H$_5$).

As a modification of the above-mentioned step, when the lithiated product is reacted with a boric acid ester as a reagent for coupling, its reaction product can be reacted with hydrofluoric acid, and then the thus-obtained reaction product is treated with, for example, potassium carbonate, cesium carbonate or tetrabutylammonium fluoride to give a compound having a salt species as M such as —BF$_3^-$K$^+$, —BF$_3^-$Cs$^+$ or —BF$_3^-$N(C$_4$H$_9$)$_4^+$.

Alternatively, the compound (5b) can be directly reacted with, for example, magnesium bromide or isopropylmagnesium bromide, without lithiation of the compound (5b), to give a compound (2b) having a species as M such as, for example, —MgBr.

The obtained compound (2b) can be isolated for use as a raw material for the production of the phenyl-substituted 1,3,5-triazine compound (1). Alternatively, the compound (2b) can be directly, i.e., without isolation, used for the production of the compound (1).

In a preferred step P-2, in view of high yield, the lithiated product is reacted with a reagent for coupling selected from dichloro(tetramethylethylenediamine)zinc(II), zinc chloride, zinc bromide, zinc iodide, trimethyltin chloride, tributyltin chloride and boric acid, to give a compound (2b) having a species as M selected from —ZnCl, —ZnBr, —ZnI, —Sn(CH$_3$)$_3$, —Sn(C$_4$H$_9$)$_3$ and —B(OH)$_2$.

The leaving group $Y^4$, includes, for example, a chlorine atom, a bromine atom, an iodine atom and a trifluoromethylsulfonyloxy group. Of these, a bromine atom and an iodine atom are preferable because the yield is high.

In the step P-2, the molar ratio of a lithium reagent to the compound (5b) is preferably in the range of 1:1 to 5:1, and especially preferably 1:1 to 3:1 in view of high yield.

In the step P-2, the reactions of the compound (5b) with the lithium reagent and suceedingly with the reagent for coupling are carried out in a reaction medium. The reaction medium includes, for example, tetrahydrofuran, toluene, benzene, diethyl ether, xylene, chloroform and dichloromethane. These reaction mediums may be used either alone or in combination. Preferably tetrahydrofuran is used alone in view of high yield.

The concentration of the compound (5b) in the step P-2 is preferably in the range of 10 mmol/L to 10,000 mmol/L, and more preferably 50 mmol/L to 200 mmol/L in view of high yield.

In the step P-2, the lithiation reaction is preferably carried out at a temperature in the range of −150° C. to −20° C., and more preferably −100° C. to −60° C. in view of high yield. The reaction time is preferably in the range of 1 minute to 3 hours, and more preferably 15 minutes to 1 hour in view of high yield.

In the step P-2, the molar ratio of a reagent for coupling to the compound (5b) is preferably in the range of 1:1 to 1:10, and especially preferably 1:1.5 to 1:3 in view of high yield.

In the step P-2, after the addition of a reagent for coupling, the reaction is preferably carried out in temperature ranges including a low temperature region of −150° C. to −20° C. and a succeeding high temperature region of −20° C. to 50° C. More preferably the reaction is carried out in temperature ranges including a low temperature region of −100° C. to −60° C. and a succeeding elevated high temperature region of 0° C. to 30° C. in view of high yield.

In the step P-2, the reaction time after the addition of the reagent for coupling varies depending the conditions such as the particular substrate and the reaction scale, and is not particularly limited. Preferably the reaction in the low temperature region is carried out in the range of 1 minute to 1 hour, and more preferably 5 minutes to 30 minutes in view of high yield. Preferably the reaction in the succeeding high temperature region is carried out in the range of 10 minutes to 10 hours, and more preferably 30 minutes to 5 hours in view of high yield.

The compound (5b) can be prepared by a coupling reaction of $Y^4$—$X^2$—$Y^4$, $Y^4$—$X^2$—$X^2$—$Y^4$, $Y^4$—$Ar^4$, $Y^4$—$X^2$—$Ar^4$, $Y^4$—$X^2$-M, $Y^4$—$X^2$—$X^2$-M, M-$Ar^4$ or M-$X^2$—$Ar^4$, using a general metal catalyst according to the method described in, for example, Tsuji: "Palladium Reagents and Catalysts", John Wiley & Sons, 2004.

The step B-1 and the step B-2 will be described. In the step B-1, the compound (2a) is reacted with the compound (3) in the presence of a metal catalyst to give the compound (4). In the step B-2, the compound (2b) is reacted with the compound (4) in the presence of a metal catalyst to give a phenyl-substituted 1,3,5-triazine compound (1) according to the present invention. The reactions in the step B-1 and the step B-2 are illustrated by the following schemes.

Step B-1

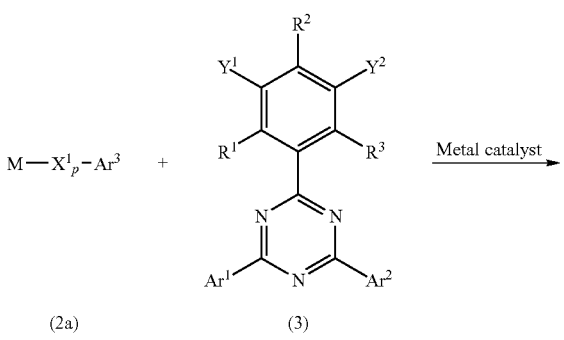

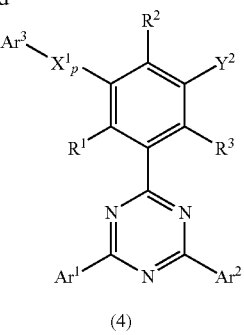

(4)

Step B-2

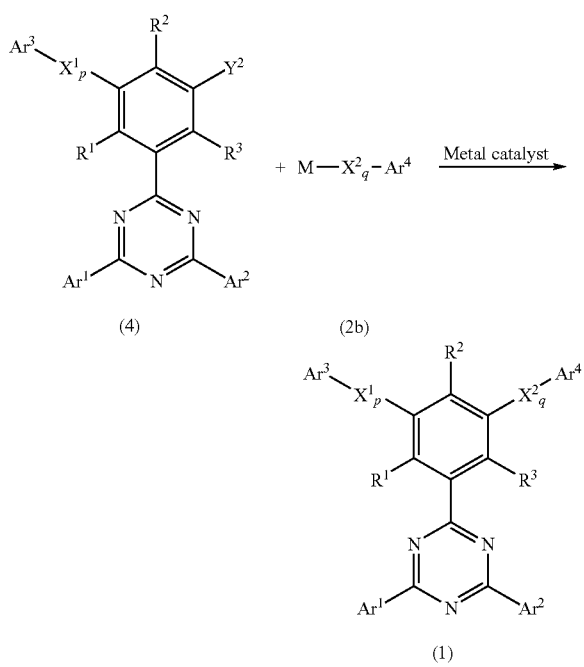

In the above formulae, M, $X^1$, p, $Ar^3$, $Ar^1$, $Ar^2$, $R^1$, $R^2$, $R^3$, $Y^1$, $Y^2$, $X^2$, q, and $Ar^4$ are the same as defined above.

As the metal catalyst used in the step B-1, those which are described with regard to the step A can be used. Such metal catalysts include, for example, a palladium catalyst, a nickel catalyst, an iron catalyst, a ruthenium catalyst, a platinum catalyst, a rhodium catalyst, an iridium catalyst, an osmium catalyst and a cobalt catalyst.

Of these, a palladium catalyst, an iron catalyst and a nickel catalyst are preferable because the yield is high. A palladium catalyst is especially preferable.

As specific examples of the palladium catalyst, those which are described with regard to the step A can be mentioned. Such metal catalysts include palladium metal such as palladium black; supported palladium metals such as palladium/alumina and palladium/carbon; palladium metal salts such as palladium chloride and palladium acetate; and complex compounds such as π-allylpalladium chloride dimmer, bis(dibenzylideneacetone)palladium, tris(dibenzylideneacetone)dipalladium, dichlorobis(triphenylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium and dichloro[1,1'-bis(diphenylphosphino)ferrocene]palladium. Of these, palladium acetate and tris(dibenzylideneacetone)dipalladium are especially preferable in view of high yield.

The above-mentioned palladium metal, palladium metal salts and palladium complex compounds may be used either alone or in combination with a tertiary phosphine.

As specific examples of the tertiary phosphine used, those which are described with regard to the step A can be mentioned. Such tertiary phosphines include, for example, triphenylphosphine, trimethylphosphine, triethylphosphine, tributylphosphine, tri(tert-butyl)phosphine, tricyclohexylphosphine, trioctylphosphine, 9,9-dimethyl-4,5-bis(diphenylphosphino)xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1'-bis(diphenylphosphino)ferrocene, (R)-(+)-2,2'-bis(diphenylphosphino)-1,1'-binaphthyl, (S)-(−)-2,2'-bis(diphenylphosphino)-1,1'-binaphthyl, 2-dicyclohexylphosphino-2',4',6'-triisopropylbiphenyl and (±)-2,2'-bis(diphenylphosphino)-1,1'-binaphthyl).

In the step B-1, the molar ratio of the compound (2a) to the compound (3) is preferably in the range of 1:0.5 to 1:5, and especially preferably 1:0.75 to 1:2 in view of high yield.

The molar ratio of the metal catalyst to the compound (3) in the step B-1 is preferably in the range of 0.001:1 to 0.5:1, and especially preferably 0.01:1 to 0.1:1 in view of high yield.

In the step B-1, the reaction is carried out in a reaction medium. The reaction medium includes, for example, methanol, ethanol, isopropyl alcohol, N,N-dimethylformamide, dioxane, diethyl ether, xylene, toluene, benzene, tetrahydrofuran, acetonitrile, dichloromethane, dimethylsulfoxide, N-methyl-2-pyrrolidone and hexamethylphosphoric triamide. These reaction mediums may be used either alone or in combination. Preferably dioxane, diethyl ether, toluene and tetrahydrofuran are used in view of high yield.

The compound (2a) produced in the step P-1 is preferably used without isolation for the step B-1 in view of high yield. In this case, the reaction medium used in the step P-1 may be used, as it is, in the step B-1.

The concentration of the compound (3) in the step B-1 is preferably in the range of 5 mmol/L to 1,000 mmol/L, and more preferably 10 mmol/L to 200 mmol/L in view of high yield.

In the step B-1, the reaction is preferably carried out at a temperature appropriately chosen in the range of 0° C. to the reflux temperature of the reaction medium used, and more preferably at the reflux temperature of the reaction medium in view of high yield.

The reaction time in the step B-1 is preferably in the range of 1 hour to 120 hours, and more preferably 6 hours to 72 hours in view of high yield.

The compound (4) can be collected by removing the reaction medium from the reaction product after completion of the step B-1. If desired, the reaction product is purified by, for example, recrystallization, column chromatography or sublimation.

The compound (4) produced in the step B-1 may be used, as it is without isolation, for the succeeding step B-2.

As the metal catalyst used in the step B-2, those which are described with regard to the step A and the step B-1 can be used. Such metal catalysts include, for example, a palladium catalyst, a nickel catalyst, an iron catalyst, a ruthenium catalyst, a platinum catalyst, a rhodium catalyst, an iridium catalyst, an osmium catalyst and a cobalt catalyst.

Of these, a palladium catalyst, an iron catalyst and a nickel catalyst are preferable because the yield is high. A palladium catalyst is especially preferable.

As specific examples of the palladium catalyst, those which are described with regard to the step A and the step B-1 can be mentioned. Such metal catalysts include palladium metal such as palladium black; supported palladium metals such as palladium/alumina and palladium/carbon; palladium metal salts such as palladium chloride and palladium acetate; and complex compounds such as π-allylpalladium chloride dimmer, bis(dibenzylideneacetone)palladium, tris(dibenzylideneacetone)dipalladium, dichlorobis(triphenylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium and dichloro[1,1'-bis(diphenylphosphino)ferrocene]palladium. Of these, palladium acetate and tris(dibenzylideneacetone) dipalladium are especially preferable in view of high yield.

The above-mentioned palladium metal, palladium metal salts and palladium complex compounds may be used either alone or in combination with a tertiary phosphine.

As specific examples of the tertiary phosphine used, those which are described with regard to the step A and the step B-1 can be mentioned. Such tertiary phosphines include, for example, triphenylphosphine, trimethylphosphine, triethylphosphine, tributylphosphine, tri(tert-butyl)phosphine, tricyclohexylphosphine, trioctylphosphine, 9,9-dimethyl-4,5-bis(diphenylphosphino)xanthene, 2-(di-tert-butylphosphino) biphenyl, 2-(dicyclohexylphosphino)biphenyl, 1,2-bis (diphenylphosphino)ethane, 1,3-bis(diphenylphosphino) propane, 1,4-bis(diphenylphosphino)butane, 1,1'-bis (diphenylphosphino)ferrocene, (R)-(+)-2,2'-bis (diphenylphosphino)-1,1'-binaphthyl, (S)-(−)-2,2'-bis (diphenylphosphino)-1,1'-binaphthyl, 2-dicyclohexylphosphino-2',4',6'-triisopropylbiphenyl and (±)-2,2'-bis(diphenylphosphino)-1,1'-binaphthyl).

In the step B-2, the molar ratio of the compound (2b) to the compound (4) is preferably in the range of 1:0.5 to 1:5, and especially preferably 1:0.75 to 1:2 in view of high yield.

The molar ratio of the metal catalyst to the compound (4) in the step B-2 is preferably in the range of 0.001:1 to 0.5:1, and especially preferably 0.01:1 to 0.1:1 in view of high yield.

In the step B-2, the reaction is carried out in a reaction medium. The reaction medium includes, for example, methanol, ethanol, isopropyl alcohol, N,N-dimethylformamide, dioxane, diethyl ether, xylene, toluene, benzene, tetrahydrofuran, acetonitrile, dichloromethane, dimethylsulfoxide, N-methyl-2-pyrrolidone and hexamethylphosphoric triamide. These reaction mediums may be used either alone or in combination. Preferably dioxane, diethyl ether, toluene and tetrahydrofuran are used in view of high yield.

The compound. (2b) produced in the step P-2 is preferably used without isolation for the step B-2 in view of high yield. In this case, the reaction medium used in the step P-2 may be used, as it is, in the step B-2.

The concentration of the compound (4) in the step B-2 is preferably in the range of 5 mmol/L to 1,000 mmol/L, and more preferably 10 mmol/L to 200 mmol/L in view of high yield.

In the step B-2, the reaction is preferably carried out at a temperature appropriately chosen in the range of 0° C. to the reflux temperature of the reaction medium used, and more preferably at the reflux temperature of the reaction medium in view of high yield.

The reaction time in the step B-2 is preferably in the range of 1 hour to 120 hours, and more preferably 6 hours to 72 hours in view of high yield.

The phenyl-substituted 1,3,5-triazine compound (1) can be collected by removing the reaction medium from a reaction mixture after completion of the step B-2. If desired, a reaction product is purified by, for example, recrystallization, column chromatography or sublimation.

The phenyl-substituted 1,3,5-triazine compound (1) can be produced from the compound (4) as a raw material by a step including the step B-2. The compound (4) is produced by a step including the step B-1.

Now a process for synthesizing the compound (3) will be described. The compound (3) can be synthesized by the process described in, for example, JP-A 2006-062962. In this process, a compound represented by the following general formula (6):

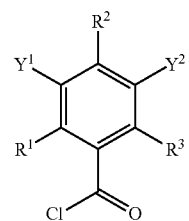

(8)

wherein $R^1$, $R^2$, $R^3$, $Y^1$ and $Y^2$ are the same as defined above, is reacted with a compound represented by the following general formula (7) and a compound represented by the following general formula (8) in the presence of a Lewis acid to give a salt represented by the following general formula (9), and then, the compound of formula (9) is treated with aqueous ammonia.

$$Ar^1\text{—}CN \qquad (7)$$

wherein $Ar^1$ is the same as defined above, $$Ar^2\text{—}CN \qquad (8)$$

wherein $Ar^2$ is the same as defined above,

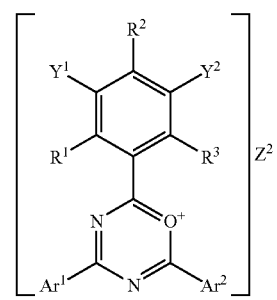

(9)

wherein $Ar^1$, $Ar^2$, $R^1$, $R^2$, $R^3$, $Y^1$ and $Y^2$ are the same as defined above, and $Z^2$ represents an anion.

In the above-mentioned synthetic process, equimolar amounts of the compound (7) and the compound (8) are employed. At a molar ratio of the sum of compound (7) and compound (8) to compound (6) varying in a broad range of 1:10 to 10:1, a good yield is obtained. However, a satisfying yield can be achieved at the stoichiometric amount ratio.

The above-mentioned reaction is carried out in a reaction medium. The reaction medium used includes, for example, chloroform, dichloromethane, 1,2-dichloroethane, carbon tetrachloride, chlorobenzene and 1,2-dichlorobenzene. In view of the yield, dichloromethane and chloroform are preferable.

As preferable examples of the Lewis acid, boron trifluoride, aluminum trichloride, iron trichloride, tin tetrachloride and antimony pentachloride can be mentioned. Antimony pentachloride is especially preferable in view of high yield.

The salt (9) produced can be isolated from the as-obtained solution containing the salt, or the as-obtained solution containing the salt can be used without isolation for the succeeding step. In the case when the salt (9) is isolated, $Z^2$ is not particularly limited provided that it is an anion. However, in view of high yield, $Z^2$ is preferably a counter ion comprising a fluoride ion or a chloride ion, which is bound to the above-mentioned Lewis acid. Such counter anion includes a tetrafluoroborate ion, a chlorotrifluoroborate ion, a tetrachloroaluminate ion, a tetrachloroferrate(III) ion, a pentachlorostannate(IV) ion and a hexachloroantimonate(V) ion.

The concentration of the aqueous ammonia used is not particularly limited, but it is preferably in the range of 5 to 50% by weight. A desired rate of reaction can be obtained with commercially available aqueous ammonia having a concentration of 28% by weight.

The reaction temperature is not particularly limited, but the reaction is preferably carried out at a temperature appropriately chosen in the range of –50° C. to the reflux temperature of the reaction medium used. The reaction time varies depending upon the particular reaction temperature, but is usually in the range of 30 minutes to 24 hours.

The compound (3) is collected by removing the reaction medium from a reaction mixture after completion of the reaction. If desired, the collected compound (3) is purified by, for example, recrystallization, column chromatography or sublimination.

The process for producing a thin film of the phenyl-substituted 1,3,5-triazine compound (1) for an organic electroluminescent is not particularly limited. For example, vacuum deposition can be adopted for the formation of the thin film. The vacuum deposition can be conducted using a conventional vacuum deposition apparatus. However, in consideration of the tact time and cost in the production of the organic electroluminescent device, the degree of vacuum at the vacuum deposition is preferably in the range of approximately $1 \times 10^{-2}$ to $1 \times 10^{-5}$ Pa which can be achieved by the conventionally used diffusion pump, turbo-molecular pump or cryopump. The rate of vacuum deposition varies depending upon the thickness of thin film, but is preferably in the range of 0.005 nm/sec to 1.0 nm/sec.

The solubility of the phenyl-substituted 1,3,5-triazine compound (1) in a solvent such as chloroform, dichloromethane, 1,2-dichloroetane, chlorobenzene, toluene, ethyl acetate or tetrahydrofuran is high. Therefore, the thin film can also be formed from a solution thereof by, for example, spin coating, ink jetting, casting or dipping using the conventional apparatus.

EXAMPLES

Now, the production of the phenyl-substituted 1,3,5-triazine compound (1) and the compound (4), according to the present invention, and the evaluation of the organic electroluminescent device having an electron transport layer comprising the phenyl-substituted 1,3,5-triazine compound (1) will be described by the following reference examples and examples, that by no means limit the scope of the invention.

Reference Example 1

Synthesis of 2-(3-bromo-5-chlorophenyl)-4,6-diphenyl-1,3,5-triazine

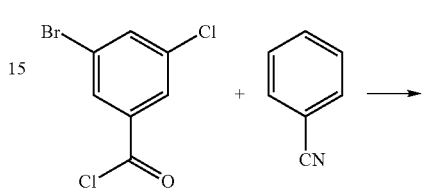

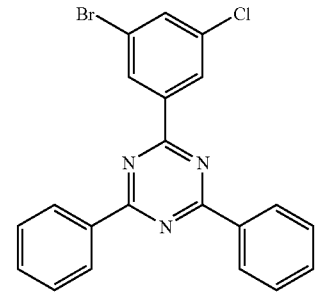

In a stream of argon, 9.1 g of 3-bromo-5-chlorobenzoyl chloride and 7.4 g of benzonitrile were dissolved in 200 mL of chloroform. To the thus-obtained solution, 10.7 g of antimony pentachloride was dropwise added at 0° C. The resultant mixture was stirred at room temperature for 1 hour, and then refluxed for 12 hours. Thereafter the mixture was cooled to room temperature, and then low boiling point ingredients were removed under a reduced pressure to give 2-(3-bromo-5-chlorphenyl)-4,6-diphenyl-oxa-3,5-diadinium hexachoroantimonate(V) as a yellow solid. The yellow solid was pulverized in a stream of argon and the thus-obtained powder was gently added to a 28% aqueous ammonia at 0° C. The thus-obtained suspension was stirred at room temperature for 1 hour. The thus-precipitated solid was collected by filtration, and was washed with water and then with methanol. The washed solid was dried and then subjected to extraction using a Soxhlet extractor (extraction solvent: tetrahydrofuran). The extracted liquid was left to stand at room temperature. The thus-precipitated solid was collected by filtration, and dried to give 5.6 g of 2-(3-bromo-5-chlorophenyl)-4,6-diphenyl-1,3,5-triazine as a white powder (Yield: 44%).

$^1$H-NMR(CDCl$_3$): δ7.57-7.70 (m, 6H), 7.75 (dd, J=1.7, 1.7 Hz, 1H), 8.66 (brs, 1H), 8.74 (d, J=7.2 Hz, 4H), 8.76 (brs, 1H)

$^{13}$C-NMR(CDCl$_3$): δ123.2, 127.7, 128.8, 129.1, 130.1, 132.9, 134.9, 135.7, 135.7, 139.5, 169.3, 172.0

Example 1

Synthesis of 2-[5-chloro-4'-(2-pyridyl)-1,1'-biphenyl-3-yl]-4,6-diphenyl-1,3,5-triazine

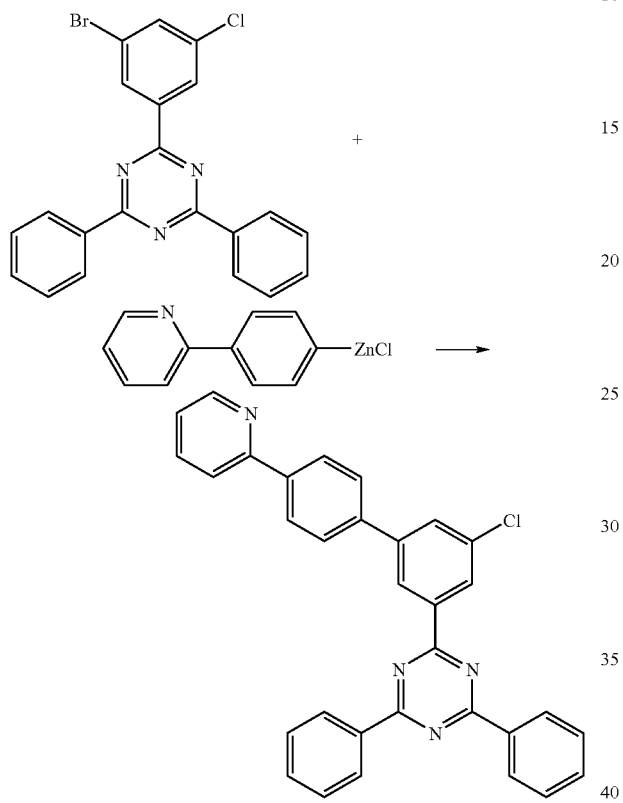

In a stream of argon, 350 mg of 2-(4-bromophenyl)pyridine was dissolved in 20 mL of tetrahydrofuran and the solution was cooled to −78° C. To the cooled solution, 1.04 mL of a solution in hexane of 1.65 mmol of butyllithium was gently added. The mixture was stirred at that temperature for 30 minutes. To this mixture, 454 mg of dichloro(tetramethylethylenediamine)zinc(II) was added. The resultant mixture was stirred at −78° C. for 10 minutes and then at room temperature for 1.5 hours.

To the mixture, 350 mg of 2-(3-bromo-5-chlorophenyl)-4,6-diphenyl-1,3,5-triazine, synthesized in Reference Example 1, and 46 mg of tetrakis(triphenylphosphine)palladium(0) were added, and the resultant mixture was refluxed under heating for 18 hours. Then the reaction mixture was left to stand at room temperature, and was concentrated under a reduced pressure to give a solid. The solid was recrystallized from dichloromethane/methanol. The thus-obtained crude product was purified by silica gel chromatography using a hexane/chloroform mixed liquid (50:50-0:100) as a developing solvent, and then again recrystallized from dichloromethane/methanol to give 339 mg of 2-[5-chloro-4'-(2-pyridyl)-1,1'-biphenyl-3-yl]-4,6-diphenyl-1,3,5-triazine as a white solid (yield: 68%).

$^1$H-NMR(CDCl$_3$): δ7.28-7.32 (m, 1H), 7.59-7.67 (m, 2H), 7.62 (d, J=7.6 Hz, 4H), 7.81-7.87 (m, 2H), 7.85 (d, J=8.3 Hz, 2H), 7.88 (brs, 1H), 8.20 (d, J=8.3 Hz, 2H), 8.74 (brs, 1H), 8.75-8.80 (m, 1H), 8.80 (d, J=7.6 Hz, 4H), 8.94 (brs, 1H)

$^{13}$C-NMR(CDCl$_3$): δ120.6, 122.4, 125.9, 127.6, 127.7, 127.8, 128.8, 129.1, 130.9, 132.8, 135.4, 136.0, 136.9, 138.6, 139.3, 140.0, 142.4, 149.9, 156.8, 171.5, 172.0

Example 2

Synthesis of 2-{4-(2-pyridyl)-[1,1':3',1"]-terphenyl-5'-yl}-4,6-diphenyl-1,3,5-triazine

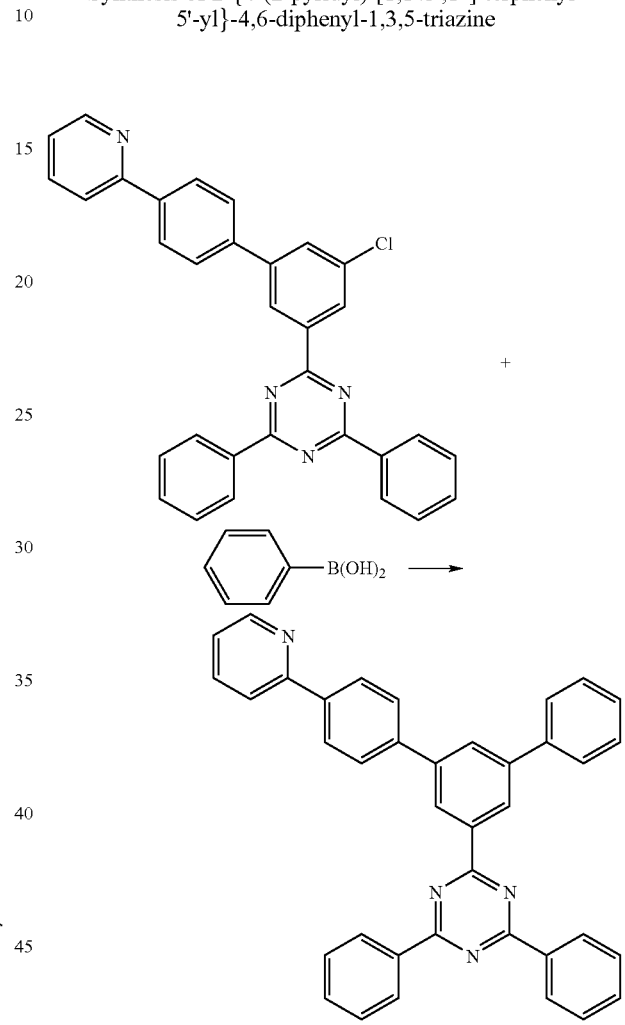

In a stream of argon, 73 mg of phenylboronic acid, 5.8 mg of tris(dibenzalacetone)dipalladium complex and 12 mg of 2-dicyclohexylphosphino-2',4',6'-triisopropylbiphenyl were suspended in 15 mL of 1,4-dioxane. 0.6 mL of an aqueous 3N potassium phosphate solution was added to the suspension, and the obtained mixture was stirred at room temperature for 10 minutes. To this mixture, 149 mg of 2-[5-chloro-4'(2-pyridyl)-1,1'-biphenyl-3-yl]-4,6-diphenyl-1,3,5-triazine, synthesized in Example 1, was added, and the resultant mixture was refluxed under heating at 110° C. for 48 hours. Then the reaction mixture was left to stand at room temperature, and was concentrated under a reduced pressure to give a solid. The solid was purified by silica gel chromatography using a hexane/chloroform mixed liquid (50:50-0:100) as a developing solvent, and then recrystallized from dichloromethane/methanol to give 162 mg of 2-{4-(2-pyridyl)-[1,1':3',1"]-terphenyl-5'-yl}-4,6-diphenyl-1,3,5-triazine as a white solid (yield: >99%).

¹H-NMR (CDCl₃): δ7.28-7.32 (m, 1H), 7.49 (brt, J=7.4 Hz, 1H) 7.56-7.72 (m, 8H), 7.80-7.89 (m, 2H), 7.85 (d, J=8.5 Hz, 2H), 7.95 (d, J=8.3 Hz, 2H), 8.12 (brs, 1H), 8.22 (d, J=8.3 Hz, 2H), 8.79 (brd, J=4.5 Hz, 1H), 8.83 (d, J=8.2 Hz, 4H), 9.02 (brs, 1H), 9.06 (brs, 1H)

¹³C-NMR (CDCl₃): δ120.5, 122.3, 126.7, 126.9, 127.5, 127.6, 127.8, 128.7, 129.0, 129.1, 130.1, 132.6, 136.2, 136.9, 137.5, 138.8, 140.9, 141.4, 141.7, 142.5, 149.9, 157.0, 171.6, 171.8

Example 3

Synthesis of 2-{4-(2-pyridyl)-[1,1':3',1"]-terphenyl-5'-yl}-4,6-diphenyl-1,3,5-triazine In a stream of argon, 73 mg of phenylboronic acid, 2.9 mg of palladium acetate, 195 mg of cesium carbonate and 12 mg of 2-dicyclohexylphosphino-2',4',6'-triisopropylbiphenyl were suspended in 15 mL of 1,4-dioxane. The obtained mixture was stirred at room temperature for 10 minutes. To this mixture, 149 mg of 2-[5-chloro-4'-(2-pyridyl)-1,1'-biphenyl-3-yl]-4,6-diphenyl-1,3,5-triazine, synthesized in Example 1, was added, and the resultant mixture was refluxed under heating at 110° C. for 48 hours. Then the reaction mixture was left to stand at room temperature, and was concentrated under a reduced pressure to give a solid. The solid was purified by silica gel chromatography using a hexane/chloroform mixed liquid (50:50-0:100) as a developing solvent, and then recrystallized from dichloromethane/methanol to give 153 mg of 2-{4-(2-pyridyl)-[1,1':3',1"]-terphenyl-5'-yl}-4,6-diphenyl-1,3,5-triazine as a white solid (yield: 95%).

Reference Example 2

Synthesis of 2-(3,5-dibromophenyl)-4,6-di-m-tolyl-1,3,5-triazine

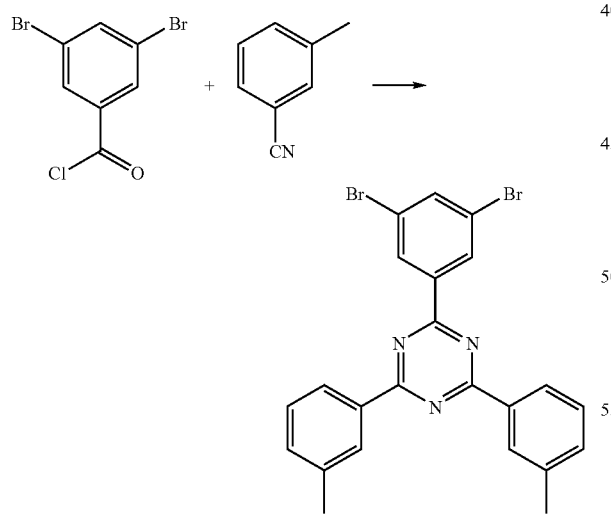

26.57 g of 3,5-dibromobenzoyl chloride and 20.85 g of 3-methylbenzonitrile were dissolved in 200 mL of chloroform. To the thus-obtained solution, 26.61 g of antimony pentachloride was dropwise added at 0° C. The resultant mixture was stirred at room temperature for 10 minutes, and then refluxed for 12 hours. Thereafter the mixture was cooled to room temperature, and then chloroform was distilled off.

The thus-obtained 2-(3,5-dibromophenyl)-4,6-di-m-tolyl-1,3,5-oxadiadinyl-1-ium hexachoroantimonate was gently added to 500 mL of a 28% aqueous ammonia at 0° C. to give a white precipitate. The white precipitate-containing liquid was stirred at room temperature for 1 hour. The white precipitate was collected by filtration, and was washed with water and then with methanol. The washed white precipitate was dried and then 200 mL of chloroform was added. The thus-obtained suspension was stirred under reflux and then filtered to collect an insoluble component. 200 mL of chloroform was added to the insoluble component, and the mixture was stirred under reflux, followed by filtration. These procedures of addition of chloroform, stirring under reflux, and filtration were repeated twice. All of the filtrates were collected, chloroform was distilled off therefrom under a reduced pressure. The thus-obtained solid was recrystallized from dichloromethane/methanol to give 26.23 g of 2-(3,5-dibromophenyl)-4,6-di-m-tolyl-1,3,5-triazine as a white solid (yield: 60%).

¹H-NMR(CDCl₃): δ2.54 (s, 6H), 7.42-7.46 (m, 2H), 7.48 (dd, J=7.5, 7.5 Hz, 2H), 7.89 (t, J=1.8 Hz, 1H), 8.52 (s, 2H), 8.54 (d, J=7.5 Hz, 2H), 8.80 (d, J=1.8 Hz, 2H)

¹³C-NMR(CDCl₃): δ21.6, 123.3, 126.3, 128.6, 129.4, 130.6, 133.7, 135.6, 137.5, 138.5, 139.8, 169.2, 172.0

Example 4

Synthesis of 2-{4,4"-bis(2-pyridyl)-[1,1':3',1"]-terphenyl-5'-yl}-4,6-di-m-tolyl-1,3,5-triazine

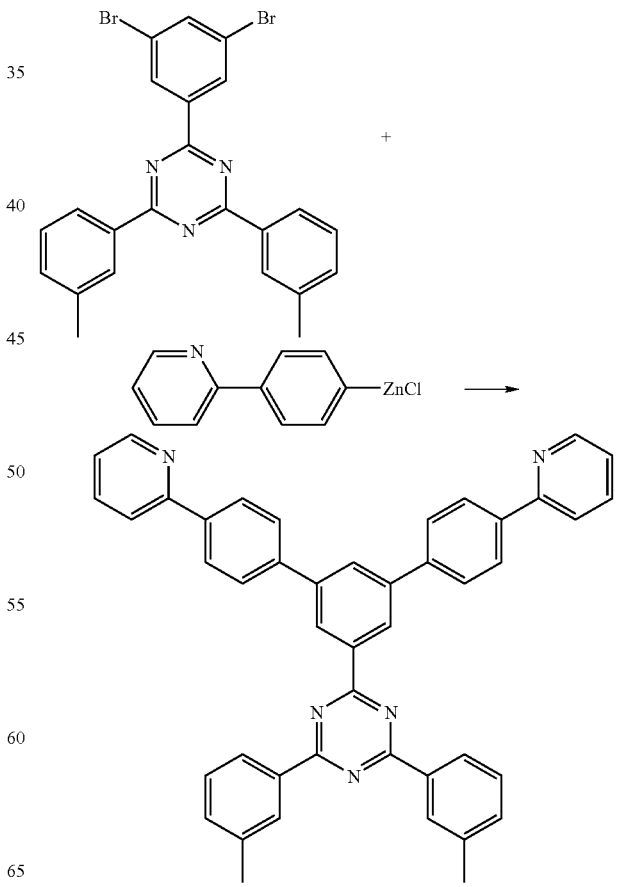

In a stream of argon, 3.51 g of 2-(4-bromophenyl)pyridine was dissolved in 80 mL of tetrahydrofuran, and the solution was cooled to −78° C. Then 10.0 mL of a solution in hexane of 15.8 mmol of butyllithium was gently added to the cooled solution. The resultant mixture was stirred at −78° C. for 20 minutes. To this mixture, 4.55 g of dichloro(tetramethylethylenediamine)zinc(II) was added. The resultant mixture was stirred at −78° C. for 10 minutes and then at room temperature for 2 hours.

To the thus-obtained solution, 2.48 g of 2-(3,5-dibromophenyl)-4,6-di-m-tolyl-1,3,5-triazine, synthesized in Reference Example 2, 0.05 g of tetrakis(triphenylphosphine)palladium(0) and 40 mL of tetrahydrofuran were added, and the resultant mixture was stirred under reflux for 17 hours. Then the reaction mixture was concentrated under a reduced pressure to give a solid. The solid was recrystallized from dichloromethane/methanol. The thus-obtained crude product was purified by silica gel chromatography using a hexane/chloroform mixed liquid (1:2—chloroform) as an eluting liquid, and then again recrystallized from dichloromethane/methanol to give 2.98 g of 2-{4,4''-bis(2-pyridyl)-[1,1':3',1'']-terphenyl-5'-yl}-4,6-di-m-tolyl-1,3,5-triazine as a white solid (yield: 93%).

$^1$H-NMR(CDCl$_3$): δ2.54 (s, 6H), 7.27 (ddd, J=7.3, 4.8, 1.1 Hz, 2H), 7.42-7.95 (m, 2H), 7.49 (dd, J=7.5, 7.5 Hz, 2H), 7.78-7.83 (m, 2H), 7.83-7.87 (m, 2H), 7.94 (d, J=8.3 Hz, 4H), 8.14 (t, J=1.7 Hz, 1H), 8.20 (d, J=8.3 Hz, 4H), 8.60 (s, 2H), 8.62 (d, J=7.5 Hz, 2H), 8.76 (brd, J=4.8 Hz, 2H), 9.04 (d, J=1.7 Hz, 2H)

$^{13}$C-NMR(CDCl$_3$): δ21.7, 120.6, 122.3, 126.4, 126.9, 127.5, 127.9, 128.7, 129.5, 129.9, 133.5, 136.2, 136.9, 137.7, 138.4, 138.9, 141.4, 141.9, 149.9, 157.0, 171.5, 172.0

Example 5

Synthesis of 2-{4,4''''-bis(2-pyridyl)-[1,1':4',1'':3'',1''':4''',1'''']-quinquephenyl-5''-yl}-4,6-di-m-tolyl-1,3,5-triazine

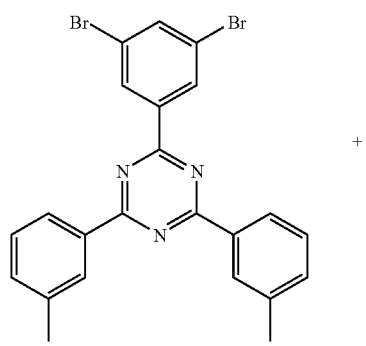

+

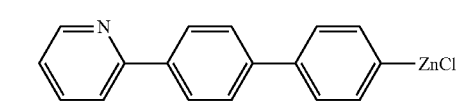

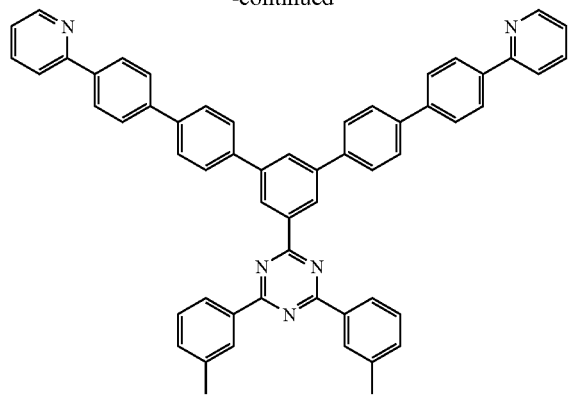

In a stream of argon, 1.32 g of 4-bromo-4'-(2-pyridyl)-biphenyl was dissolved in 120 mL of tetrahydrofuran, and the solution was cooled to −78° C. Then, 2.9 mL of a solution in hexane of 4.5 mmol of butyllithium was gently added to the cooled solution. The resultant mixture was stirred at −78° C. for 20 minutes. To this mixture, 1.29 g of dichloro(tetramethylethylenediamine)zinc(II) was added. The resultant mixture was stirred at −78° C. for 10 minutes and then at room temperature for 2 hours.

To the thus-obtained solution, 0.70 g of 2-(3,5-dibromophenyl)-4,6-di-m-tolyl-1,3,5-triazine, synthesized in Reference Example 2, and 0.035 g of tetrakis(triphenylphosphine)palladium(0) were added, and the resultant mixture was stirred under reflux for 14 hours. Then the reaction mixture was concentrated under a reduced pressure to give a solid. The solid was recrystallized from dichloromethane/methanol. The thus-obtained crude product was purified by silica gel chromatography using a hexane/chloroform mixed liquid (1:1—chloroform) as an eluting liquid, and then again recrystallized from toluene to give 0.97 g of 2-{4,4''''-bis(2-pyridyl)-[1,1':4',1'':3'',1''':4''',1'''']-quinquephenyl-5''-yl}-4,6-di-m-tolyl-1,3,5-triazine as a white solid (yield: 86%).

$^1$H-NMR(CDCl$_3$): δ2.55 (s, 6H), 7.24-7.29 (m, 2H), 7.43-7.47 (m, 2H), 7.50 (dd, J=7.5, 7.5 Hz, 2H), 7.76-7.84 (m, 4H), 7.84 (d, J=8.3 Hz, 4H), 7.87 (d, J=8.3 Hz, 4H), 7.93 (d, =8.3 Hz, 4H), 8.12-8.17 (m, 1H), 8.15 (d, J=8.3 Hz, 4H), 8.61 (s, 2H), 8.63 (d, J=7.5 Hz, 2H), 8.74 (brd, J=4.6 Hz, 2H), 9.04 (d, J=1.7 Hz, 2H)

$^{13}$C-NMR(CDCl$_3$): δ21.7, 120.5, 122.2, 126.4, 126.7, 127.5, 127.7, 128.0, 128.7, 129.5, 129.9, 133.5, 136.3, 136.8, 137.7, 138.4, 138.6, 140.0, 140.1, 141.1, 141.9, 149.8, 157.1, 171.6, 172.0

Reference Example 3

Synthesis of 2-(3,5-dibromophenyl)-4,6-diphenyl-1,3,5-triazine

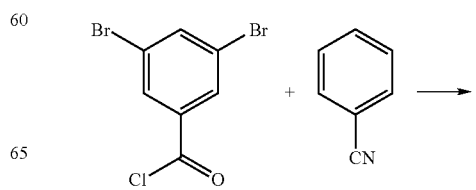

-continued

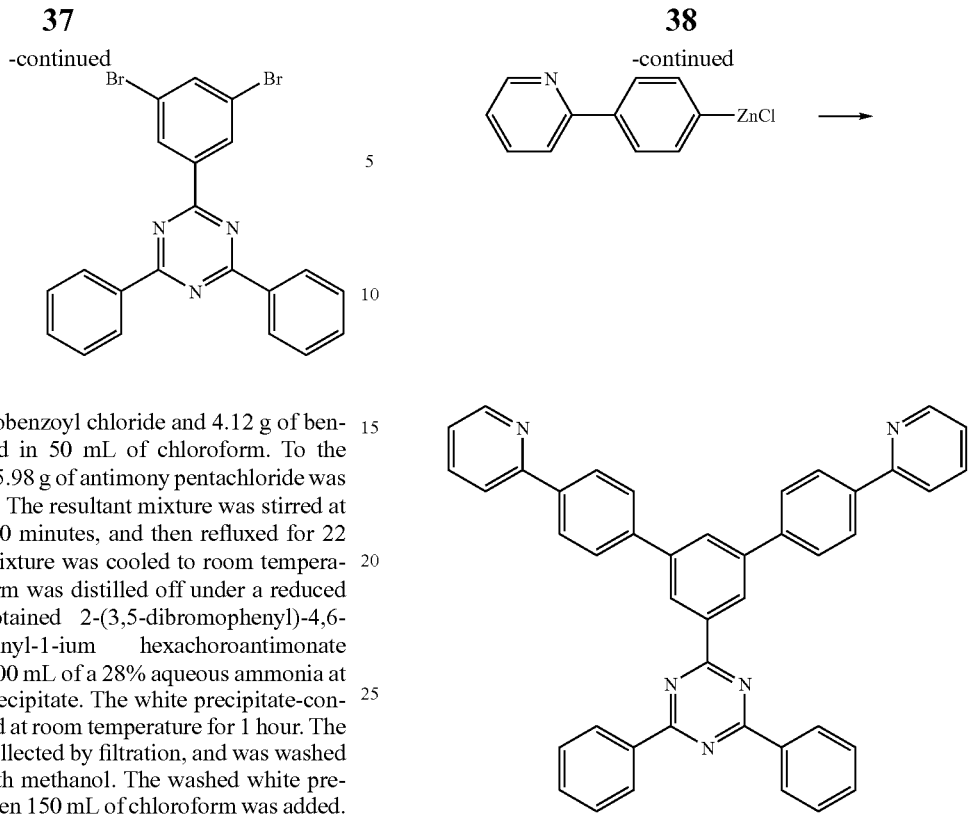

5.97 g of 3,5-dibromobenzoyl chloride and 4.12 g of benzonitrile were dissolved in 50 mL of chloroform. To the thus-obtained solution, 5.98 g of antimony pentachloride was dropwise added at 0° C. The resultant mixture was stirred at room temperature for 10 minutes, and then refluxed for 22 hours. Thereafter the mixture was cooled to room temperature, and then chloroform was distilled off under a reduced pressure. The thus-obtained 2-(3,5-dibromophenyl)-4,6-diphenyl-1,3,5-oxadiadinyl-1-ium hexachoroantimonate was gently added into 300 mL of a 28% aqueous ammonia at 0° C. to give a white precipitate. The white precipitate-containing liquid was stirred at room temperature for 1 hour. The white precipitate was collected by filtration, and was washed with water and then with methanol. The washed white precipitate was dried and then 150 mL of chloroform was added. The thus-obtained suspension was stirred under reflux and then filtered to collect an insoluble component. 100 mL of chloroform was added to the insoluble component, and then the mixture was stirred under reflux, followed by filtration. These procedures of addition of chloroform, stirring under reflux, and filtration were repeated twice. All of the filtrates were collected, chloroform was distilled off therefrom under a reduced pressure. The thus-obtained solid was recrystallized from dichloromethane/methanol to give 6.32 g of 2-(3, 5-dibromophenyl)-4,6-diphenyl-1,3,5-triazine as a white solid (yield: 68%).

$^1$H-NMR(CDCl$_3$): δ7.56-7.61 (m, 4H), 7.61-7.67 (m, 2H), 7.90 (t, J=1.8 Hz, 1H), 8.72-8.78 (m, 4H), 8.82 (d, J=1.8 Hz, 2H)

$^{13}$C-NMR(CDCl$_3$): δ123.4, 128.8, 129.1, 130.6, 133.0, 135.7, 137.6, 139.8, 169.3, 172.0

Example 6

Synthesis of 2,4-diphenyl-6-{4,4''-bis(2-pyridyl)-[1,1':3',1'']-terphenyl-5'-yl}-1,3,5-triazine

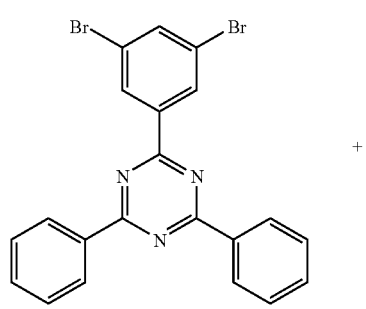

In a stream of argon, 2.81 g of 2-(4-bromophenyl)pyridine was dissolved in 50 mL of tetrahydrofuran, and the solution was cooled to −78° C. Then, 8.2 mL of a solution in hexane of 13.0 mmol of butyllithium was gently added to the cooled solution. The resultant mixture was stirred at −78° C. for 20 minutes. To this mixture, 3.64 g of dichloro(tetramethylethylenediamine)zinc(II) was added. The resultant mixture was stirred at −78° C. for 10 minutes and then at room temperature for 2 hours.

To the thus-obtained solution, 1.87 g of 2-(3,5-dibromophenyl)-4,6-diphenyl-1,3,5-triazine, synthesized in Reference Example 3, 0.046 g of tetrakis(triphenylphosphine)palladium(0), and 50 mL of tetrahydrofuran were added, and the resultant mixture was stirred under reflux for 19 hours. Then the reaction mixture was concentrated under a reduced pressure to give a solid. The solid was recrystallized from dichloromethane/methanol. The thus-obtained crude product was purified by silica gel chromatography using a hexane/chloroform mixed liquid (1:2—chloroform) as an eluting liquid, and then again recrystallized from dichloromethane/methanol and then from toluene to give 2.14 g of 2,4-diphenyl-6-[4,4''-bis(2-pyridyl)-[1,1':3',1'']-terphenyl-5'-yl]-1,3,5-triazine as a white solid (yield: 87%).

$^1$H-NMR(CDCl$_2$): δ7.25 (ddd, J=7.2, 4.8, 1, 2 Hz, 2H), 7.57-7.67 (m, 6H), 7.78-7.82 (m, 2H), 7.82-7.86 (m, 2H), 7.94 (d, J=8.3 Hz, 4H), 8.15 (t, J=1.7 Hz, 1H), 8.20 (d, J=8.3 Hz, 4H), 8.76 (brd, J=4.8 Hz, 2H), 8.79-8.85 (m, 4H), 9.05 (d, J=1.7 Hz, 2H)

$^{13}$C-NMR(CDCl$_3$): δ120.6, 122.3, 126.9, 127.5, 127.9, 128.8, 129.1, 129.9, 132.7, 136.2, 136.9, 137.5, 138.9, 141.3, 141.9, 149.9, 157.0, 171.5, 171.8

Reference Example 4

Synthesis of 2-(3,5-dibromophenyl)-4,6-bis(4-tert-butylphenyl)-1,3,5-triazine

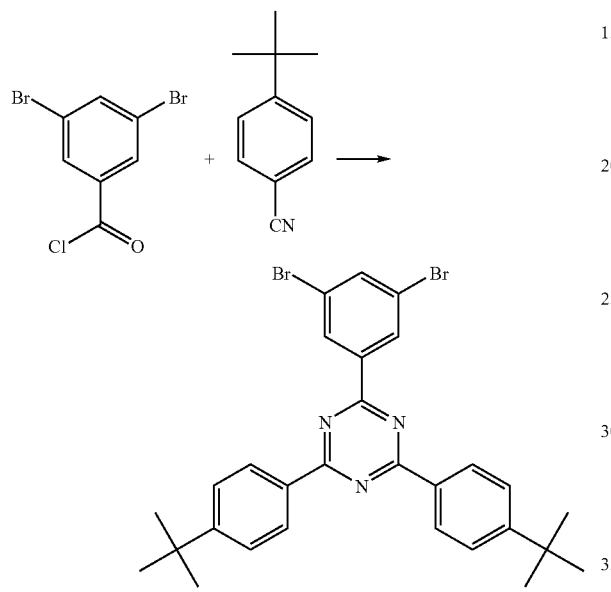

2.98 g of 3,5-dibromobenzoyl chloride and 3.18 g of 4-tert-butylbenzonitrile were dissolved in 30 mL of chloroform. To the thus-obtained solution, 2.99 g of antimony pentachloride was dropwise added at 0° C. The resultant mixture was stirred at room temperature for 10 minutes, and then refluxed for 17 hours. Thereafter the mixture was cooled to room temperature, and then chloroform was distilled off under a reduced pressure. The thus-obtained 2-(3,5-dibromophenyl)-4,6-bis(4-tert-butylphenyl)-1,3,5-oxadiadinyl-1-ium hexachoroantimonate was gently added to 200 mL of a 28% aqueous ammonia at 0° C. to give a white precipitate. The white precipitate-containing liquid was stirred at room temperature for 1 hour. The white precipitate was collected by filtration, and was washed with water and then with methanol. The washed white precipitate was dried and then 150 mL of chloroform was added. The thus-obtained suspension was stirred under reflux and then filtered to collect an insoluble component. 100 mL of chloroform was added to the insoluble component, and then the mixture was stirred under reflux, followed by filtration. All of the filtrates were collected, chloroform was distilled of therefrom under a reduced pressure. The thus-obtained solid was recrystallized from dichloromethane/methanol to give 4.46 g of 2-(3,5-dibromophenyl)-4,6-bis(4-tert-butylphenyl)-1,3,5-triazine as a white solid (yield: 77%).

$^1$H-NMR(CDCl$_3$): δ1.41 (8,18H), 7.61 (d, J=8.5 Hz, 4H), 7.88 (t, J=1.8 Hz, 1H), 8.65 (d, J=8.5 Hz, 4H), 8.80 (d, J=1.8 Hz, 2H)

$^{13}$C-NMR(CDCl$_3$): δ31.2, 35.1, 123.3, 125.7, 128.9, 130.5, 133.1, 137.4, 140.0, 156.5, 169.0, 171.8

Example 7

Synthesis of 2,4-bis(4-tert-butylphenyl)-6-{4,4''-bis(2-pyridyl)-[1,1':3',1'']-terphenyl-5'-yl}-1,3,5-triazine

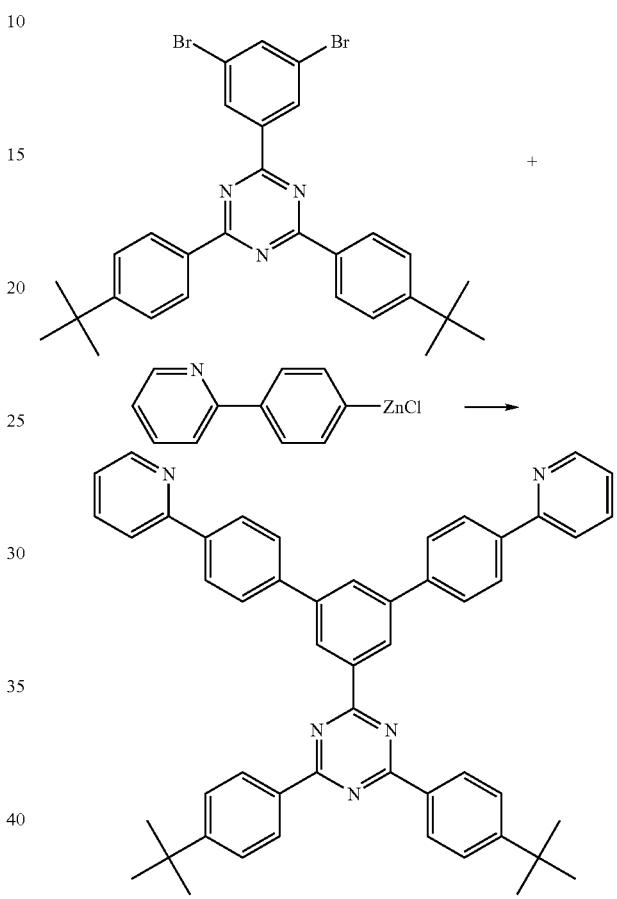

In a stream of argon, 2.81 g of 2-(4-bromophenyl)pyridine was dissolved in 50 mL of tetrahydrofuran, and the solution was cooled to −78° C. Then, 8.2 mL of a solution in hexane of 13.0 mmol of butyllithum was gently added to the cooled solution. The resultant mixture was stirred at −78° C. for 20 minutes. To this mixture, 3.64 g of dichloro(tetramethylethylenediamine)zinc(II) was added. The resultant mixture was stirred at −78° C. for 10 minutes and then at room temperature for 2 hours.

To the thus-obtained solution, 2.32 g of 2-(3,5-dibromophenyl)-4,6-bis(4-tert-butylphenyl)-1,3,5-triazine, synthesized in Reference Example 4, 0.046 g of tetrakis(triphenylphosphine)palladium(0), and 20 mL of tetrahydrofuran were added, and the resultant mixture was stirred under reflux for 22 hours. Then the reaction mixture was concentrated under a reduced pressure to give a solid. The solid was recrystallized from dichloromethane/methanol. The thus-obtained crude product was purified by silica gel chromatography using a hexane/chloroform mixed liquid (1:2-1:3) as an eluting liquid, and then again recrystallized from dichloromethane/methanol to give 2.59 g of 2,4-bis(4-tert-butylphenyl)-6-{4,4''-bis(2-pyridyl)-[1,1':3',1'']-terphenyl-5'-yl}-1,3,5-triazine as a white solid (yield: 89%).

¹H-NMR(CDCl₃): δ1.42 (s, 18H), 7.25-7.30 (m, 2H), 7.62 (d, J=8.4 Hz, 4H), 7.78-7.83 (m, 2H), 7.83-7.88 (m, 2H), 7.94 (d, J=8.2 Hz, 4H), 8.15 (t, J=1.7 Hz, 1H), 8.20 (d, J=8.2 Hz, 4H), 8.73 (d, J=8.4 Hz, 4H), 8.76 (brd, J=4.8 Hz, 2H), 9.05 (d, J=1.7 Hz, 2H)

¹³C-NMR(CDCl₃): δ31.3, 35.2, 120.5, 122.3, 125.7, 126.8, 127.5, 127.8, 128.9, 129.7, 133.6, 136.8, 137.8, 138.8, 141.4, 141.8, 149.9, 156.2, 157.0, 171.3, 171.7

Reference Example 5

Synthesis of 2,4-bis(biphenyl-4-yl)-6-(3,5-dibromophenyl)-1,3,5-triazine

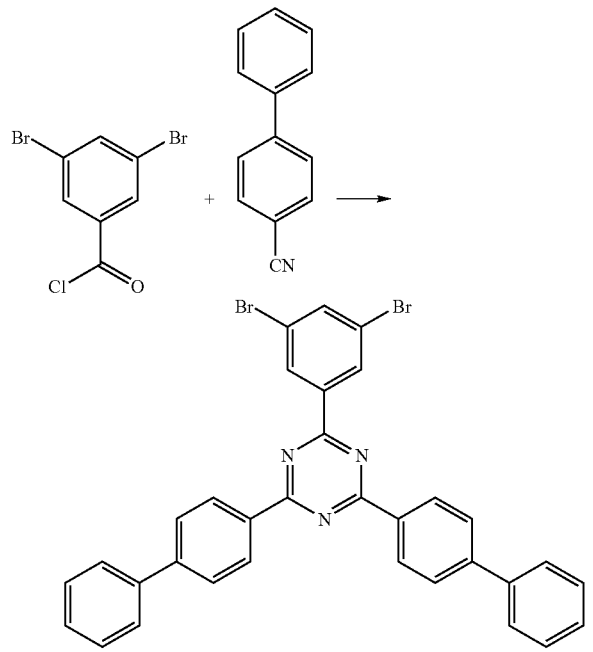

2.98 g of 3,5-dibromobenzoyl chloride and 3.58 g of 4-biphenylcarbonitrile were dissolved in 40 mL of chloroform. To the thus-obtained solution, 2.99 g of antimony pentachloride was dropwise added at 0° C. The resultant mixture was stirred at room temperature for 10 minutes, and then refluxed for 14 hours. Thereafter the mixture was cooled to room temperature, and then chloroform was distilled off under a reduced pressure. The thus-obtained 2,4-bis(biphenyl-4-yl)-6-(3,5-dibromophenyl)-1,3,5-oxadiadinyl-1-ium hexachoroantimonate was gently added to 150 mL of a 28% aqueous ammonia at 0° C. to give a white precipitate. The white precipitate-containing liquid was stirred at room temperature for 1 hour. The white precipitate was collected by filtration, and was washed with water and then with methanol. The washed white precipitate was dried and then 200 mL of chloroform was added. The thus-obtained suspension was stirred under reflux and then filtered to collect an insoluble component. 150 mL of chloroform was added to the insoluble component, and then the mixture was stirred under reflux, followed by filtration. These procedures of addition of chloroform, stirring under reflux, and filtration were repeated twice. All of the filtrates were collected, chloroform was distilled off therefrom under a reduced pressure. The thus-obtained solid was recrystallized from dichloromethane/methanol to give 5.14 g of 2,4-bis(biphenyl-4-yl)-6-(3,5-dibromophenyl)-1,3,5-triazine as a white solid (yield: 83%).

¹H-NMR(CDCl₃): δ7.40-7.45 (m, 2H), 7.49-7.54 (m, 4H), 7.70-7.75 (m, 4H), 7.83 (d, J=8.5 Hz, 4H), 7.91 (t, J=1.8 Hz, 1H), 8.83 (d, J=8.5 Hz, 4H), 8.85 (d, J=1.8 Hz, 2H)

¹³C-NMR(CDCl₃): δ123.4, 127.3, 127.5, 128.2, 129.0, 129.7, 130.7, 134.7, 137.6, 139.9, 140.3, 145.7, 169.3, 171.8

Synthesis of 2,4-diphenyl-6-{4,4''-bis(2-pyridyl)-[1,1':3',1'']-terphenyl-5'-yl}-1,3,5-triazine Example 8

Synthesis of 2,4-bis(biphenyl-4-yl)-6-{4,4''-bis(2-pyridyl)-[1,1':3',1'']-terphenyl-5'-yl}-1,3,5-triazine

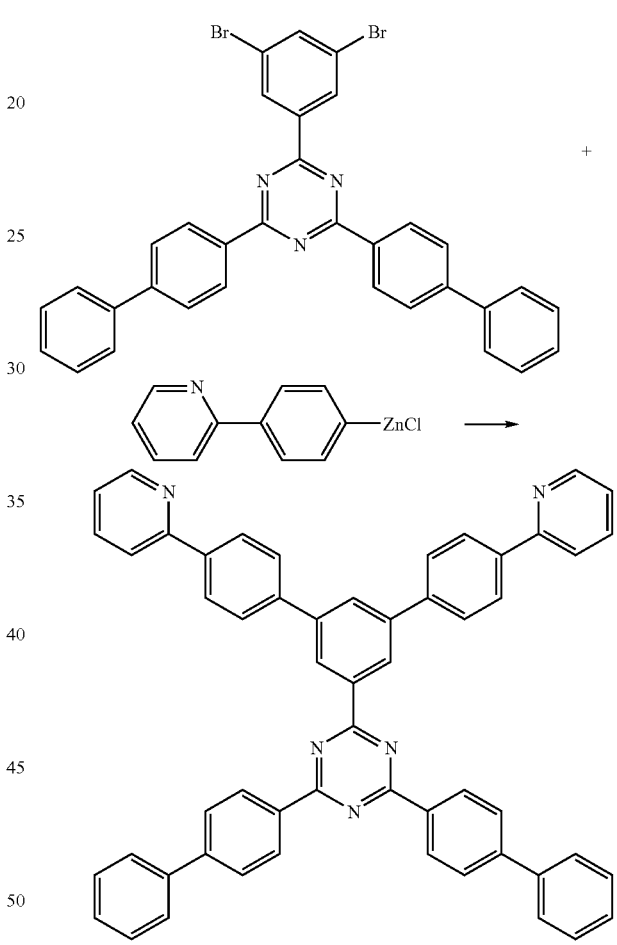

In a stream of argon, 2.11 g of 2-(4-bromophenyl)pyridine was dissolved in 50 mL of tetrahydrofuran, and the solution was cooled to −78° C. Then, 6.0 mL of a solution in hexane of 9.5 mmol of butyllithium was gently added to the cooled solution. The resultant mixture was stirred at −78° C. for 20 minutes. To this mixture, 2.73 g of dichloro(tetramethylethylenediamine)zinc(II) was added. The resultant mixture was stirred at −78° C. for 10 minutes and then at room temperature for 2 hours.

To the thus-obtained solution, 1.86 g of 2,4-bis(biphenyl-4-yl)-6-(3,5-dibromophenyl)-1,3,5-triazine, synthesized in Reference Example 5, 0.069 g of tetrakis(triphenylphosphine)palladium(0), and 30 mL of tetrahydrofuran were added, and the resultant mixture was stirred under reflux for 18 hours. Then the reaction mixture was concentrated under a reduced pressure to give a solid. The solid was recrystallized from dichloromethane/methanol. The thus-obtained crude product was subjected to extraction using a Soxhlet extractor (extraction solvent: chloroform). The extracted liquid was left to stand at room temperature. The thus-precipitated solid was collected by filtration, and dried to give 1.33 g of 2,4-bis(biphenyl-4-yl)-6-{4,4"-bis(2-pyridyl)-[1,1':3',1"]-terphenyl-5'-yl}-1,3,5-triazine as a white solid (Yield: 58%).

$^1$H-NMR (CDCl$_3$): δ7.23-7.33 (m, 2H), 7.40-7.45 (m, 2H), 7.49-7.55 (m, 4H), 7.71-7.76 (m, 4H), 7.80-7.90 (m, 4H), 7.85 (d, J=8.5 Hz, 4H), 7.97 (d, J=8.3 Hz, 4H), 8.18 (t, J=1.7 Hz, 1H), 8.23 (d, J=8.3 Hz, 4H), 8.77 (brd, J=4.5 Hz, 2H), 8.91 (d, J=8.5 Hz, 4H), 9.09 (d, J=1.7 Hz, 2H)

Reference Example 6

Synthesis of 2-(3,5-dibromophenyl)-4,6-bis(1-naphthyl)-1,3,5-triazine

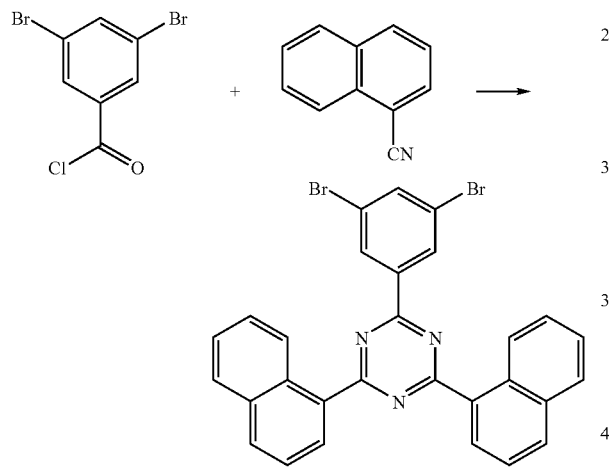

2.98 g of 3,5-dibromobenzoyl chloride and 3.06 g of 1-naphthonitrile were dissolved in 30 mL of chloroform. To the thus-obtained solution, 2.99 g of antimony pentachloride was dropwise added at 0° C. The resultant mixture was stirred at room temperature for 10 minutes, and then refluxed for 22 hours. Thereafter the mixture was cooled to room temperature, and then chloroform was distilled off under a reduced pressure. The thus-obtained 2-(3,5-dibromophenyl)-4,6-bis(1-naphthyl)-1,3,5-oxadiadinyl-1-ium hexachoroantimonate was gently added to 100 mL of a 28% aqueous ammonia at 0° C. to give a white precipitate. The white precipitate-containing liquid was stirred at room temperature for 1 hour. The white precipitate was collected by filtration, and was washed with water and then with methanol. The washed white precipitate was dried and then purified by silica gel chromatography using a hexane/chloroform mixed liquid (3:1-1:1) as an eluting liquid, and then recrystallized from dichloromethane/methanol to give 1.73 g of 2-(3,5-dibromophenyl)-4,6-bis(1-naphthyl)-1,3,5-triazine as a white solid (yield: 29%).

$^1$H-NMR(CDCl$_3$): δ7.60 (ddd, J=8.0, 6.8, 1.2 Hz, 2H), 7.65 (ddd, J=8.6, 6.8, 1.5 Hz, 2H), 7.69 (dd, J=8.1, 7.4 Hz, 2H), 7.92 (t, J=1.8 Hz, 1H), 7.99 (brd, J=8.0 Hz, 2H), 8.11 (brd, J=8.1 Hz, 2H), 8.58 (dd, J=7.4, 1.3 Hz, 2H), 8.84 (d, J=1.8 Hz, 2H), 9.16 (brd, J=8.6 Hz, 2H)

$^{13}$C-NMR(CDCl$_3$): δ123.6, 125.2, 125.9, 126.3, 127.5, 128.8, 130.7, 131.1, 131.3, 132.8, 133.3, 134.3, 137.8, 139.7, 168.9, 174.5

Example 9

Synthesis of 2,4-bis(1-naphthyl)-6-{4,4"-bis(2-pyridyl)-[1,1':3',1"]-terphenyl-5'-yl}-1,3,5-triazine

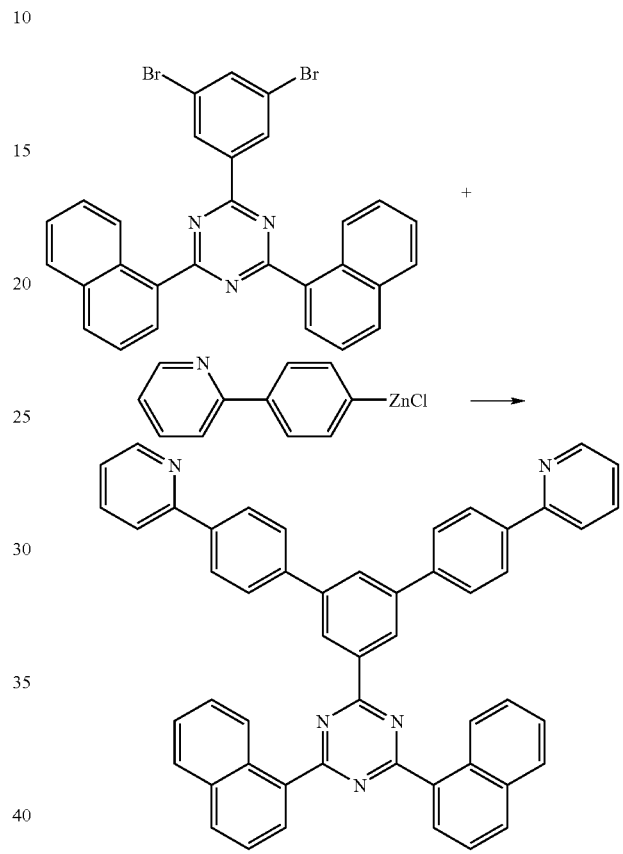

In a stream of argon, 1.40 g of 2-(4-bromophenyl)pyridine was dissolved in 30 mL of tetrahydrofuran, and the solution was cooled to −78° C. Then, 4.0 mL of a solution in hexane of 6.3 mmol of butyllithium was gently added to the cooled solution. The resultant mixture was stirred at −78° C. for 20 minutes. To this mixture, 1.82 g of dichloro(tetramethylethylenediamine)zinc(II) was added. The resultant mixture was stirred at −78° C. for 10 minutes and then at room temperature for 2 hours.

To the thus-obtained solution, 1.13 g of 2-(3,5-dibromophenyl)-4,6-bis(1-naphthyl)-1,3,5-triazine, synthesized in Reference Example 6, 0.046 g of tetrakis(triphenylphosphine)palladium(0), and 30 mL of tetrahydrofuran were added, and the resultant mixture was stirred under reflux for 19 hours. Then the reaction mixture was concentrated under a reduced pressure to give a solid. The solid was recrystallized from dichloromethane/methanol. The thus-obtained crude product was purified by silica gel chromatography using a hexane/chloroform mixed liquid (2:3—chloroform) as an eluting liquid. The purified product was again recrystallized from dichloromethane/methanol and then sublimed to give 1.12 g of 2,4-bis(1-naphthyl)-6-{4,4"-bis(2-pyridyl)-[1,1':3',1"]-terphenyl-5'-yl}-1,3,5-triazine as a white solid (Yield: 78%).

1H-NMR(CDCl3): δ7.27 (ddd, J=7.1, 4.8, 1.4 Hz, 2H), 7.60 (ddd, J=8.0, 6.8, 1.2 Hz, 2H), 7.66 (ddd, J=8.6, 6.8, 1.5 Hz, 2H), 7.69 (dd, J=8.1, 7.2 Hz, 2H), 7.76-7.81 (m, 2H), 7.81-7.85 (m, 2H), 7.94 (d, J=8.5 Hz, 4H), 7.99 (brd, J=8.0 Hz, 2H), 8.11 (brd, J=8.1 Hz, 2H), 8.18 (d, J=8.5 Hz, 4H), 8.21 (t, J=1.7 Hz, 1H), 8.65 (dd, J=7.2, 1.2 Hz, 2H), 8.75 (ddd, J=4.8, 1.7, 1.0 Hz, 2H), 9.11 (d, J=1.7 Hz, 2H), 9.33 (d, J=8.6 Hz, 2H)

13C-NMR(CDCl3): δ120.5, 122.2, 125.2, 126.2, 126.8, 127.3, 127.5, 127.7, 128.8, 130.0, 131.0, 131.4, 132.6, 133.7, 134.3, 136.8, 137.4, 138.8, 141.0, 141.9, 149.8, 156.9, 171.1, 174.3

Reference Example 7

Synthesis of 2-(3,5-dibromophenyl)-4,6-bis(biphenyl-3-yl)-1,3,5-triazine

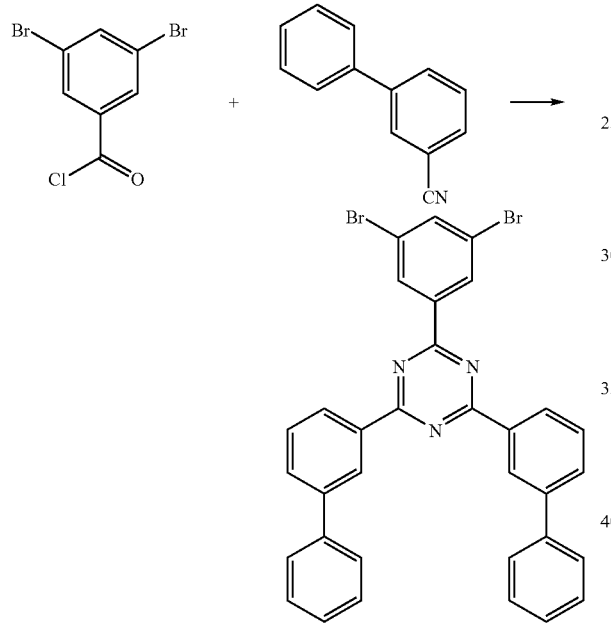

4.1 g of 3,5-dibromobenzoyl chloride and 5.0 g of 3-phenylbenzonitrile were dissolved in 100 mL of chloroform in an argon atmosphere. To the thus-obtained solution, 4.2 g of antimony pentachloride was dropwise added at 0° C. The resultant mixture was stirred at room temperature for 1 hour, and then refluxed for 12 hours. Thereafter the mixture was cooled to room temperature, and then low boiling point components were removed under a reduced pressure to give 2-(3,5-dibromophenyl)-4,6-bis(biphenyl-3-yl)-oxa-3,5-diadinium hexachoroantimonate(V) as a red solid. The red solid was pulverized into a powder in a stream of argon, and the powder was gently added to a 28% aqueous ammonia at 0° C. The thus-obtained suspension was stirred at room temperature for 1 hour. The thus-precipitated solid was collected by filtration, and was washed with water and then with methanol. The washed solid was dried and then subjected to extraction using a Soxhlet extractor (extraction solvent: chloroform). The extracted liquid was left to stand at room temperature. The thus-precipitated solid was collected by filtration, and dried to give 2.8 g of 2-(3,5-dibromophenyl)-4,6-bis(biphenyl-3-yl)-1,3,5-triazine as a white powder (yield: 32%).

1H-NMR (CDCl3): δ7.46 (brt, J=7.4 Hz, 2H), 7.52-7.58 (m, 4H), 7.67 (dd, J=7.8, 7.7 Hz, 2H), 7.76 (brd, J=7.7 Hz, 4H), 7.86 (d, J=7.7 Hz, 2H), 7.90 (brd, 1H), 8.72 (d, J=7.8 Hz, 2H), 8.81 (d, J=1.8 Hz, 2H), 8.95 (s, 2H)

13C-NMR(CDCl3): δ123.4, 127.4, 127.7, 127.8, 128.1, 130.7, 131.7, 136.2, 137.7, 139.7, 140.7, 141.9, 169.4, 172.0

Example 10

Synthesis of 2,4-bis(biphenyl-3-yl)-6-{4,4"-bis(2-pyridyl)-[1,1':3',1"]-terphenyl-5'-yl}-1,3,5-triazine

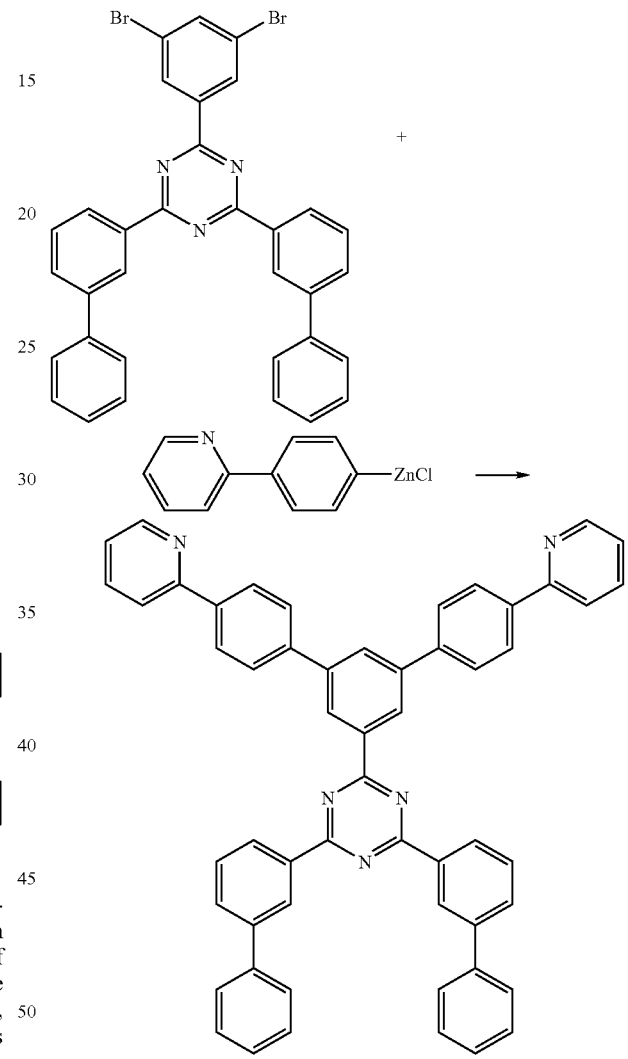

In a stream of argon, 1.38 g of 2-(4-bromophenyl)pyridine was dissolved in 100 mL of tetrahydrofuran, and the solution was cooled to −78° C. Then, 3.99 mL of a solution in hexane of 6.30 mmol of butyllithum was gently added to the cooled solution. The resultant mixture was stirred at that temperature for 30 minutes. To this mixture, 1.82 g of dichloro(tetramethylethylenediamine)-zinc (II) was added. The resultant mixture was stirred at −78° C. for 10 minutes and then at room temperature for 1.5 hours.

To the thus-obtained solution, 1.24 g of 2-(3,5-dibromophenyl)-4,6-bis(biphenyl-3-yl)-1,3,5-triazine, synthesized in Reference Example 7, and 0.185 g of tetrakis-(triphenylphosphine)palladium (0) were added, and the resultant mixture was refluxed under heating for 18 hours. Then the reaction mixture was left to stand at room temperature. Then the reaction mixture was concentrated under a reduced pressure to give a solid. The solid was recrystallized from dichloromethane/methanol. The thus-obtained crude product was purified by silica gel chromatography using a hexane/chloroform mixed liquid (50:50-0:100) as a developing solvent. The purified product was again recrystallized from hot toluene to give 1.08 g of 2,4-bis(biphenyl-3-yl)-6-{4,4''-bis(2-pyridyl)-[1,1':3',1'']-terphenyl-5'-yl}-1,3,5-triazine as a white solid (Yield: 70%).

$^1$H-NMR(CDCl$_3$): δ7.30-7.35 (m, 2H), 7.43-7.49 (m, 2H), 7.56 (dd, J=7.8, 7.6 Hz, 4H), 7.72 (dd, J=7.7, 7.7 Hz, 2H), 7.80 (d, J=7.8 Hz, 4H), 7.82-7.93 (m, 6H), 7.98 (d, J=8.3 Hz, 4H), 8.21 (t, J=1.7 Hz, 1H), 8.23 (d, J=8.3 Hz, 4H), 8.79 (d, J=4.9 Hz, 2H), 8.83 (d, J=7.7 Hz, 2H), 9.09 (s, 2H), 9.10 (d, J=1.7 Hz, 2H)

$^{13}$C-NMR (CDCl$_3$): δ120.6, 122.3, 126.9, 127.4, 127.6, 127.7, 127.8, 127.8, 128.1, 129.0, 129.3, 130.1, 131.4, 136.8, 136.9, 137.6, 138.9, 140.8, 141.3, 141.8, 141.9, 149.9, 157.0, 171.7, 171.9

Example 11

Synthesis of 2-[3,5-di(pyridin-2-yl)phenyl]-4,6-di-m-tolyl-1,3,5-triazine

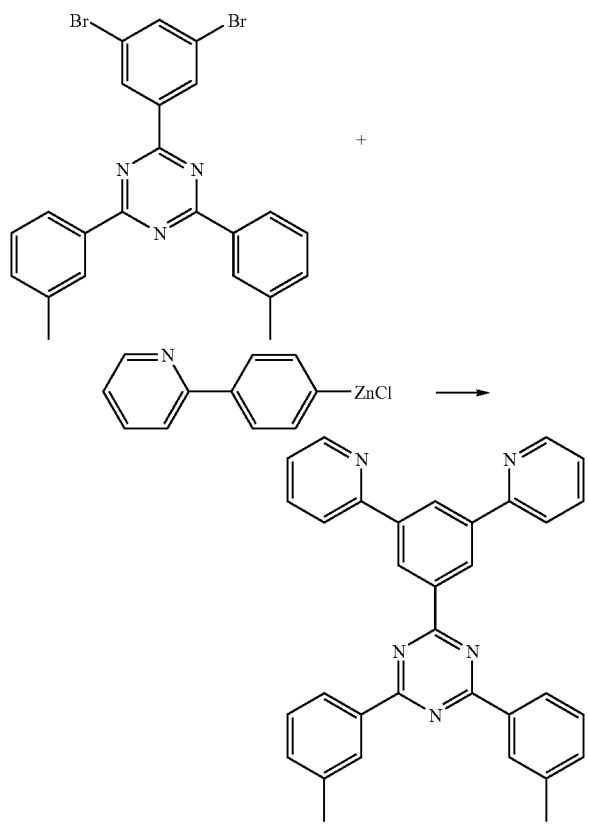

In a stream of argon, 2.37 g of 2-bromopyridine was dissolved in 100 mL of tetrahydrofuran, and the solution was cooled to −78° C. Then, 20.4 mL of a solution in hexane of 32.0 mmol of tert-butyllithium was gently added to the cooled solution. The resultant mixture was stirred at −78° C. for 20 minutes. To this mixture, 4.54 g of dichloro(tetramethylethylenediamine) zinc(II) was added. The resultant mixture was stirred at −78° C. for 10 minutes and then at room temperature for 2 hours.

To the thus-obtained solution, 2.48 g of 2-(3,5-dibromophenyl)-4,6-di-m-tolyl-1,3,5-triazine, synthesized in Reference Example 2, and 0.231 g of tetrakis(triphenylphosphine)-palladium(0) were added, and the resultant mixture was stirred under reflux for 22 hours. Then the reaction solution was concentrated under a reduced pressure to give a solid. The solid was recrystallized from dichloromethane/methanol. The thus-obtained crude product was purified by silica gel chromatography using a hexane/chloroform mixed liquid (1:3-0:100) as an eluting liquid, and then again recrystallized from dichloromethane/-methanol to give 1.01 g of 2-[3,5-di(pyridin-2-yl)phenyl]-4,6-di-m-tolyl-1,3,5-triazine as a white solid (yield: 41%).

$^1$H-NMR(CDCl$_3$): δ2.46 (s, 6H), 7.24 (ddd, J=7.6, 4.7, 0.8 Hz, 2H), 7.35 (m, 2H), 7.41 (dd, J=7.5, 7.5 Hz, 2H), 7.78 (ddd, J=7.8, 7.6, 1.8 Hz, 2H), 7.93 (brd, J=7.8 Hz, 2H), 8.53 (s, 2H), 8.55 (d, J=7.5 Hz, 2H), 8.73 (brd, J=4.7 Hz, 2H), 8.86 (t, J=11.7 Hz, 1H), 9.31 (d, J=1.7 Hz, 2H)

$^{13}$C-NMR(CDCl$_3$): δ21.7, 121.1, 122.6, 126.4, 127.9, 128.6, 129.6, 129.8, 133.4, 136.3, 136.9, 137.7, 138.4, 140.7, 149.9, 157.0, 171.5, 171.9

Example 12

Manufacture of an Organic Electroluminescent Device Comprising 2-{4,4''-bis(2-pyridyl)-[1,1':3',1'']-terphenyl-5'-yl}-4,6-di-m-tolyl-1,3,5-triazine, and Evaluation of the Properties Thereof A glass substrate with an indium-tin oxide (ITO) transparent electrode was prepared, which had a stripe pattern comprised of ITO film with a 2 mm width. The substrate was washed with isopropyl alcohol and then surface-treated by irradiation of ultraviolet rays and generation of ozone. Using the surface-treated substrate, an organic electroluminescent device with an emitting area of 4 mm$^2$ having a multilayer structure as shown in FIG. 1 was manufactured as follows. Each layer was formed by vacuum deposition. The glass substrate was placed in a vacuum deposition chamber, and the inner pressure was reduced to 1.0×10$^{-4}$ Pa. On the glass substrate 1, organic compound layers, i.e., a hole injection layer 2, a hole transport layer 3, an emitting layer 4 and an electron transport layer 5 were formed in this order. Further a cathode layer 6 was formed. The hole injection layer 2 was formed by vacuum-depositing phtalocyanine copper (II), previously purified by sublimation, into a thickness of 25 nm. The hole transport layer 3 was formed by vacuum-depositing N,N'-di(naphthylen-1-yl)-N,N'-diphenylbenzidine (NPD) into a thickness of 45 nm.

The emitting layer 4 was formed by vacuum-depositing a mixture of 99 wt. % of 4,4'-bis(2,2-diphenyl-ethen-1-yl) diphenyl (DPVBi) and 1 wt. % of 4,4'-bis[4-(di-p-tolylamino)styryl]biphenyl (DPAVBi) into a thickness of 40 nm. The electron transport layer 5 was formed by vacuum-depositing 2-{4,4''-bis(2-pyridyl)-[1,1':3',1'']-terphenyl-5'-yl}-4,6-di-m-tolyl-1,3,5-triazine, synthesized in Example 4, into a thickness of 20 nm.

The vacuum deposition of each organic material was conducted by subjecting each organic material to electric resistance heating to form a thin film, and vacuum depositing the hot thin film at a deposition rate of 0.3 to 0.5 nm/sec.

Then, a metal mask was arranged so as to be orthogonal to the ITO stripe and a cathode layer 6 was vacuum-deposited. The vacuum deposition of the cathode layer 6 was conducted so as to have a double layer structure comprising a lithium fluoride layer with a thickness of 0.5 nm and an aluminum layer with a thickness of 100 nm. The measurement of thickness of each organic material thin film layer was conducted by stylus profilometer ("DEKTAK").

Finally the thus-obtained assembly of multi-layers was encapsulated with a glass cap and ultraviolet ray-curable epoxy resin (available from Nagase Chemtex Corporation). The encapsulation was conducted in a nitrogen atmosphere having an oxygen-and-moisture content of below 1 ppm within a glove box.

Luminous properties of the thus-manufactured organic electroluminescent device were evaluated by applying a direct current using a luminance meter BM-9 available from Topcon Corporation. The luminous properties as measured at a current density of 20 mA/cm² were as follows. Voltage 5.4 V, luminance 1,529 cd/m², current efficiency 7.7 cd/A, power efficiency 4.5 lm/W. Luminance half-life of the device was 83 hours with a voltage increase of +1.9 V.

Example 13

By the same procedures as adopted in Example 12, an organic electroluminescent device was manufactured except that an emitting layer 4 was formed by vacuum-depositing tris(8-quinolinolato)aluminum(III)(Alq) into a thickness of 40 nm instead of the emitting layer formed in Example 12.

The device exhibited a voltage of 4.7 V, a luminance of 839 cd/m², a current efficiency of 4.2 cd/A, and a power efficiency of 2.8 lm/W. Luminance half-life of the device was 2,800 hours with a voltage increase of +1.2 V.

Example 14

By the same procedures as adopted in Example 12, an organic electroluminescent device was manufactured except that an electron transport layer 5 was formed by vacuum-depositing 2,4-diphenyl-6-{4,4"-bis(2-pyridyl)-[1,1':3',1"]-terphenyl-5'-yl}-1,3,5-triazine, synthesized in Example 6, into a thickness of 20 nm instead of the electron transport layer formed in Example 12.

The device exhibited a voltage of 5.9 V, a luminance of 1,136 cd/m², a current efficiency of 5.7 cd/A, and a power efficiency of 3.8 lm/W. Luminance half-life of the device was 64 hours with a voltage increase of +1.8 V.

Example 15

By the same procedures as adopted in Example 13, an organic electroluminescent device was manufactured except that an electron transport layer 5 was formed by vacuum-depositing 2,4-diphenyl-6-{4,4"-bis(2-pyridyl)-[1,1':3',1"]-terphenyl-5'-yl}-1,3,5-triazine into a thickness of 20 nm instead of the electron transport layer formed in Example 13.

The device exhibited a voltage of 4.5 V, a luminance of 797 cd/m², a current efficiency of 4.0 cd/A, and a power efficiency of 2.8 lm/W. Luminance half-life of the device was 2,500 hours with a voltage increase of +1.2 V.

Example 16

By the same procedures as adopted in Example 12, an organic electroluminescent device was manufactured except that an electron transport layer 5 was formed by vacuum-depositing 2,4-bis(biphenyl-4-yl)-6-{4,4"-bis(2-pyridyl)-[1,1':3',1"]-terphenyl-5'-yl}-1,3,5-triazine, synthesized in Example 8, into a thickness of 20 nm instead of the electron transport layer formed in Example 12.

The device exhibited a voltage of 6.4 V, a luminance of 1,193 cd/m², a current efficiency of 5.9 cd/A, and a power efficiency of 3.0 lm/W. Luminance half-life of the device was 57 hours with a voltage increase of +1.9 V.

Example 17

By the same procedures as adopted in Example 13, an organic electroluminescent device was manufactured except that an electron transport layer 5 was formed by vacuum-depositing 2,4-bis(biphenyl-4-yl)-6-{4,4"-bis(2-pyridyl)-[1,1':3',1"]-terphenyl-5'-yl}-1,3,5-triazine into a thickness of 20 nm instead of the electron transport layer formed in Example 13.

The device exhibited a voltage of 4.3 V, a luminance of 823 cd/m², a current efficiency of 4.1 cd/A, and a power efficiency of 3.0 lm/W. Luminance half-life of the device was 2,500 hours with a voltage increase of +1.7 V.

Comparative Example 1

By the same procedures as adopted in Example 12, an organic electroluminescent device was manufactured except that an electron transport layer 5 with a thickness of 20 nm was formed by vacuum-depositing tris(8-quinolinolato)aluminum (III) (Alq), which is the conventional electron transport material, instead of 2-{4,4"-bis(2-pyridyl)-[1,1':3',1"]-terphenyl-5'-yl}-4,6-di-m-tolyl-1,3,5-triazine used in Example 12.

The device exhibited a voltage of 6.9 V, a luminance of 1,223 cd/m², a current efficiency of 6.1 cd/A, and a power efficiency of 2.8 lm/W. Luminance half-life of the device was 53 hours with a voltage increase of +3.1 V.

Comparative Example 2

By the same procedures as adopted in Example 13, an organic electroluminescent device was manufactured except that an electron transport layer 5 with a thickness of 20 nm was formed by vacuum-depositing tris(8-quinolinolato)aluminum (III) (Alq), which is the conventional electron transport material, instead of 2-{4,4"-bis(2-pyridyl)-[1,1':3',1"]-terphenyl-5'-yl}-4,6-di-m-tolyl-1,3,5-triazine used in Example 13.

The device exhibited a voltage of 5.4 V, a luminance of 857 cd/m², a current efficiency of 4.3 cd/A, and a power efficiency of 2.5 lm/W. Luminance half-life of the device was 1,785 hours with a voltage increase of +2.5 V.

Example 18

Synthesis of 2,4-bis(2-naphthyl)-6-{4,4"-bis(2-pyridyl)-[1,1':3',1"]-terphenyl-5'-yl}-1,3,5-triazine

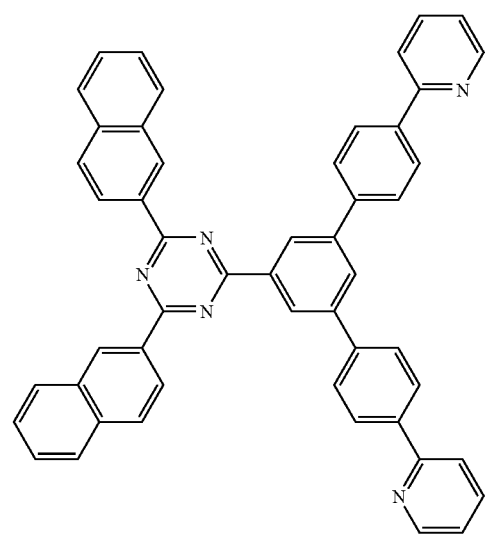

$C_{51}H_{33}N_5$
Exact Mass: 715.27
Mol. Wt.: 715.84
C, 85.57; H, 4.65; N, 9.78

In a stream of argon, 1.40 g of 2-(4-bromophenyl)pyridine was dissolved in 30 mL of tetrahydrofuran, and the solution was cooled to −78° C. Then, 3.9 mL of a solution in hexane of 6.30 mmol of butyllithium was gently added to the cooled solution. The resultant mixture was stirred at −78° C. for 20 minutes. To this mixture, 1.82 g of dichloro(tetramethylethylenediamine)zinc(II) was added. The resultant mixture was stirred at −78° C. for 10 minutes and then at room temperature for 2 hours.

To the thus-obtained solution, 1.13 g of 2-(3,5-dibromophenyl)-4,6-bis(2-naphthyl)-1,3,5-triazine and 0.046 g of tetrakis(triphenylphosphine)palladium(0), and 50 mL of tetrahydrofuran were added, and the resultant mixture was stirred under reflux for 15 hours. Then the reaction mixture was concentrated under a reduced pressure to give a solid. The solid was recrystallized from dichloromethane/methanol. The thus-obtained crude product was purified by silica gel chromatography using a hexane/chloroform mixed liquid (1:1—chloroform) as an eluting liquid. The purified product was again recrystallized from dichloromethane/methanol to give 1.15 g of 2,4-bis(2-naphthyl)-6-{4,4"-bis(2-pyridyl)-[1,1':3',1"]-terphenyl-5'-yl}-1,3,5-triazine as a white solid (Yield: 80%).

$^1$H-NMR(CDCl$_3$): δ7.32 (ddd, J=7.3, 4.8, 1.1 Hz, 2H), 7.60-7.68 (m, 4H), 7.82-7.87 (m, 2H), 7.88-7.91 (m, 2H), 7.97-8.01 (m, 2H), 8.01 (d, J=8.3 Hz, 4H), 8.09 (brd, J=8.6 Hz, 2H), 8.16-8.20 (m, 2H), 8.21 (t, J=1.7 Hz, 1H), 8.26 (d, J=8.3 Hz, 4H), 8.81 (brd, J=4.8 Hz, 2H), 8.93 (dd, J=8.6, 1.6 Hz, 2H), 9.16 (d, J=1.7 Hz, 2H), 9.43 (brs, 2H).

$^{13}$C-NMR(CDCl$_3$): δ120.6, 122.3, 125.3, 126.5, 126.9, 127.6, 127.9, 128.0, 128.5, 129.8, 130.0, 130.2, 133.2, 133.6, 135.8, 136.9, 137.6, 138.8, 141.4, 141.8, 149.9, 157.0, 171.5, 171.8.

Example 19

Synthesis of 2,4-bis-biphenyl-3-yl-6-[3,5-bis(2-pyridyl)-phenyl]-1,3,5-triazine

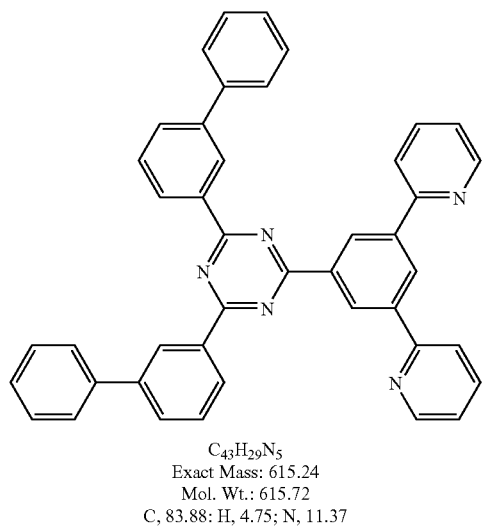

C$_{43}$H$_{29}$N$_5$
Exact Mass: 615.24
Mol. Wt.: 615.72
C, 83.88; H, 4.75; N, 11.37

In a stream of argon, 11.2 mL of a solution in pentane of 17.7 mmol of tert-butyllithum was gently added to 40 mL of tetrahydrofuran, previously cooled to −78° C. To this solution, 1.37 g of 2-bromopyridine was dropwise added. The resultant mixture was stirred at −78° C. for 30 minutes. To this mixture, 2.63 g of dichloro(tetramethylethylenediamine) zinc (II) was added. The resultant mixture was stirred at −78° C. for 10 minutes and then at room temperature for 2 hours.

To the thus-obtained solution, 1.78 g of 2,4-bis(biphenyl-3-yl)-6-(3,5-dibromophenyl)-1,3,5-triazine and 0.069 g of tetrakis(triphenylphosphine)palladium(0), dissolved in 20 mL of tetrahydrofuran, were added, and the resultant mixture was stirred under reflux for 15 hours. Then the reaction mixture was concentrated under a reduced pressure to give a solid. The solid was recrystallized from dichloromethane/methanol. The thus-obtained crude product was purified by silica gel chromatography using a hexane/chloroform mixed liquid (1:1—chloroform) as an eluting liquid. The purified product was again recrystallized from dichloromethane/methanol to give 1.16 g of 2,4-bis-biphenyl-3-yl-6-[3,5-bis(2-pyridyl)phenyl]-1,3,5-triazine as a white solid (Yield: 65%).

$^1$H-NMR(CDCl$_3$): δ7.31 (brdd, J=7.3, 4.9 Hz, 2H), 7.40-7.46 (m, 2H), 7.49-7.56 (m, 4H), 7.64 (brdd, J=7.7, 7.7 Hz, 2H), 7.74-7.79 (m, 4H), 7.80-7.87 (m, 4H), 7.98 (brd, J=7.7 Hz, 2H), 8.75-8.82 (m, 4H), 8.93 (t, J=1.7 Hz, 1H), 9.04 (brdd, J=1.6, 1.6 Hz, 2H), 9.40 (d, J=1.7 Hz, 2H).

$^{13}$C-NMR(CDCl$_3$): δ121.3, 122.6, 127.4, 127.7, 127.8, 127.9, 128.1, 129.0, 129.2, 129.8, 131.3, 136.7, 136.9, 137.3, 140.6, 140.8, 141.6, 149.9, 156.8, 171.5, 171.7.

Example 20

By the same procedures as adopted in Example 12, an organic electroluminescent device was manufactured except that an electron transport layer 5 was formed by vacuum-depositing 2,4-bis(4-tert-butylphenyl)-6-{4,4"-bis(2-pyridyl)-[1,1':3',1"]-terphenyl-5'-yl}-1,3,5-triazine, synthesized in Example 7, into a thickness of 20 nm instead of the electron transport layer formed in Example 12.

The device exhibited a voltage of 5.7 V, a luminance of 2,150 cd/m$^2$, a current efficiency of 10.2 cd/A, and a power efficiency of 5.7 lm/W. Luminance half-life of the device was 103 hours with a voltage increase of +1.9 V.

Example 21

By the same procedures as adopted in Example 13, an organic electroluminescent device was manufactured except that an electron transport layer 5 was formed by vacuum-depositing 2,4-bis(4-tert-butylphenyl)-6-{4,4"-bis(2-pyridyl)-[1,1':3',1"]-terphenyl-5'-yl}-1,3,5-triazine into a thickness of 20 nm instead of the electron transport layer formed in Example 13.

The device exhibited a voltage of 5.0 V, a luminance of 989 cd/m$^2$, a current efficiency of 4.9 cd/A, and a power efficiency of 3.1 lm/W. Luminance half-life of the device was 3,500 hours with a voltage increase of +1.5 V.

Example 22

By the same procedures as adopted in Example 12, an organic electroluminescent device was manufactured except that an electron transport layer 5 was formed by vacuum-depositing 2-{4,4""-bis(2-pyridyl)-[1,1':4',1":3",1'":4'",1""]-quinquephenyl-5"-yl}-4,6-di-m-tolyl-1,3,5-triazine, synthesized in Example 5, into a thickness of 20 nm instead of the electron transport layer formed in Example 12.

The device exhibited a voltage of 5.4 V, a luminance of 961 cd/m, a current efficiency of 5.9 cd/A, and a power efficiency of 3.0 lm/W. Luminance half-life of the device was 55 hours with a voltage increase of +1.7 V.

Example 23

By the same procedures as adopted in Example 13, an organic electroluminescent device was manufactured except that an electron transport layer 5 was formed by vacuum-depositing 2-{4,4''''-bis(2-pyridyl)-[1,1':4',1'':3'',1''':4''',1'''']-quinquephenyl-5''-yl}-4,6-di-m-tolyl-1,3,5-triazine into a thickness of 20 nm instead of the electron transport layer formed in Example 13.

The device exhibited a voltage of 4.4 V, a luminance of 912 cd/m$^2$, a current efficiency of 4.6 cd/A, and a power efficiency of 2.9 lm/W. Luminance half-life of the device was 2,400 hours with a voltage increase of +1.5 V.

Example 24

By the same procedures as adopted in Example 12, an organic electroluminescent device was manufactured except that an electron transport layer 5 was formed by vacuum-depositing 2,4-bis(1-naphthyl)-6-{4,4''-bis(2-pyridyl)-[1,1':3',1'']-terphenyl-5'-yl}-1,3,5-triazine, synthesized in Example 9, into a thickness of 20 nm instead of the electron transport layer formed in Example 12.

The device exhibited a voltage of 6.4 V, a luminance of 1,992 cd/m$^2$, a current efficiency of 9.0 cd/A, and a power efficiency of 4.8 lm/W. Luminance half-life of the device was 108 hours with a voltage increase of +1.5 V.

Example 25

By the same procedures as adopted in Example 13, an organic electroluminescent device was manufactured except that an electron transport layer 5 was formed by vacuum-depositing 2,4-bis(1-naphthyl)-6-{4,4''-bis(2-pyridyl)-[1,1':3',1'']-terphenyl-5'-yl}-1,3,5-triazine into a thickness of 20 nm instead of the electron transport layer formed in Example 13.

The device exhibited a voltage of 4.9 V, a luminance of 957 cd/m$^2$, a current efficiency of 4.8 cd/A, and a power efficiency of 3.0 lm/W. Luminance half-life of the device was 2,500 hours with a voltage increase of +1.4 V.

Example 26

By the same procedures as adopted in Example 12, an organic electroluminescent device was manufactured except that an electron transport layer 5 was formed by vacuum-depositing 2,4-bis(biphenyl-3-yl)-6-{4,4''-bis(2-pyridyl)-[1,1':3',1'']-terphenyl-5'-yl}-1,3,5-triazine, synthesized in Example 10, into a thickness of 20 nm instead of the electron transport layer formed in Example 12.

The device exhibited a voltage of 6.0 V, a luminance of 1,780 cd/m$^2$, a current efficiency of 8.0 cd/A, and a power efficiency of 4.0 lm/W. Luminance half-life of the device was 58 hours with a voltage increase of +1.6 V.

Example 27

By the same procedures as adopted in Example 13, an organic electroluminescent device was manufactured except that an electron transport layer 5 was formed by vacuum-depositing 2,4-bis(biphenyl-3-yl)-6-{4,4''-bis(2-pyridyl)-[1,1':3',1'']-terphenyl-5'-yl}-1,3,5-triazine into a thickness of 20 nm instead of the electron transport layer formed in Example 13.

The device exhibited a voltage of 4.2 V, a luminance of 886 cd/m$^2$, a current efficiency of 3.8 cd/A, and a power efficiency of 2.9 lm/W. Luminance half-life of the device was 2,300 hours with a voltage increase of +1.2 V.

Example 28

By the same procedures as adopted in Example 12, an organic electroluminescent device was manufactured except that an electron transport layer 5 was formed by vacuum-depositing 2,4-bis(2-naphthyl)-6-{4,4''-bis(2-pyridyl)-[1,1':3',1'']-terphenyl-5'-yl}-1,3,5-triazine, synthesized in Example 18, into a thickness of 20 nm instead of the electron transport layer formed in Example 12.

The device exhibited a voltage of 6.6 V, a luminance of 1,940 cd/m$^2$, a current efficiency of 9.7 cd/A, and a power efficiency of 4.3 lm/W. Luminance half-life of the device was 89 hours with a voltage increase of +1.6 V.

Example 29

By the same procedures as adopted in Example 13, an organic electroluminescent device was manufactured except that an electron transport layer 5 was formed by vacuum-depositing 2,4-bis(2-naphthyl)-6-{4,4''-bis(2-pyridyl)-[1,1':3',1'']-terphenyl-5'-yl}-1,3,5-triazine into a thickness of 20 nm instead of the electron transport layer formed in Example 13.

The device exhibited a voltage of 4.4 V, a luminance of 835 cd/m$^2$, a current efficiency of 4.2 cd/A, and a power efficiency of 3.0 lm/W. Luminance half-life of the device was 3,100 hours with a voltage increase of +1.5 V.

Example 30

By the same procedures as adopted in Example 12, an organic electroluminescent device was manufactured except that an electron transport layer 5 was formed by vacuum-depositing 2,4-bis-biphenyl-3-yl-6-[3,5-bis(2-pyridyl)-phenyl]-1,3,5-triazine, synthesized in Example 19, into a thickness of 20 nm instead of the electron transport layer formed in Example 12.

The device exhibited a voltage of 5.8 V, a luminance of 2,240 cd/m$^2$, a current efficiency of 9.9 cd/A, and a power efficiency of 5.7 lm/W. Luminance half-life of the device was 79 hours with a voltage increase of +1.9 V.

Example 31

By the same procedures as adopted in Example 13, an organic electroluminescent device was manufactured except that an electron transport layer 5 was formed by vacuum-depositing 2,4-bis-biphenyl-3-yl-6-[3,5-bis(2-pyridyl)-phenyl]-1,3,5-triazine into a thickness of 20 nm instead of the electron transport layer formed in Example 13.

The device exhibited a voltage of 4.9 V, a luminance of 915 cd/m$^2$, a current efficiency of 4.6 cd/A, and a power efficiency of 3.0 lm/W. Luminance half-life of the device was 2,400 hours with a voltage increase of +1.7 V.

INDUSTRIAL APPLICABILITY

A film comprised of a phenyl-substituted 1,3,5-triazine compound according to the present invention has outstanding properties in surface smoothness, amorphousness, heat resistance, electron transportability, hole blocking capability, resistance to oxidation and reduction, moisture resistance, oxygen resistance and electron injection property. Therefore, said film is useful as a material for an organic electroluminescent device, especially as a material for an electron transport layer, a hole blocking layer and a light emitting host layer of an organic electroluminescent device.

An electroluminescent device comprising the phenyl-substituted 1,3,5-triazine compound exhibits a sufficiently reduced driving voltage and a high efficiency, a long service life, and a minimized increase in voltage, as shown in the working examples mentioned above. Utilizing these outstanding properties, the organic electroluminescent device has a wide use including, for example, a display panel and a luminaire. The organic electroluminescent is expected to exhibit beneficial effects such as, for example, a reduction of power consumption, leading to minimization in deterioration of a battery; an enhanced efficiency leading to minimization in heat build-up; prolongation in service life; and a minimized increase in voltage, leading to reduction in load on driving circuits.

The invention claimed is:

1. A phenyl-substituted 1,3,5-triazine compound of formula (1):

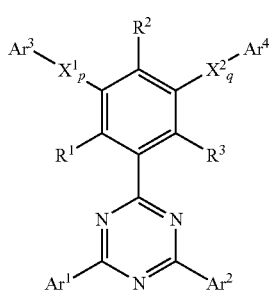

(1)

wherein:
Ar$^1$ and Ar$^2$ each independently represent a phenyl group, a naphthyl group or a biphenylyl group, wherein these groups may have one or more substituents selected from an alkyl group having 1 to 6 carbon atoms and a trifluoromethyl group;
R$^1$, R$^2$ and R$^3$ each independently represent a hydrogen atom or a methyl group;
X$^1$ and X$^2$ each independently represent a phenylene group, a naphthylene group or a pyridylene group, wherein these groups may have one or more substituents selected from an alkyl group having 1 to 4 carbon atoms and a fluorine atom;
p and q each independently represent an integer in the range of 0 to 2, wherein, when p is 2, the adjacent X$^1$s may be the same or different, and when q is 2, the adjacent X$^2$s may be the same or different; and
Ar$^3$ and Ar$^4$ each independently represent a pyridyl group which may have one or more substituents selected from an alkyl group having 1 to 4 carbon atoms and a fluorine atom, or a phenyl group which may have one or more substituents selected from an alkyl group having 1 to 4 carbon atoms and a fluorine atom.

2. The phenyl-substituted 1,3,5-triazine compound according to claim 1, wherein either one or both of Ar$^3$ and Ar$^4$ represent a pyridyl group which may have one or more substituents selected from an alkyl group having 1 to 4 carbon atoms and a fluorine atom.

3. A process for producing a phenyl-substituted 1,3,5-triazine compound of formula (1a):

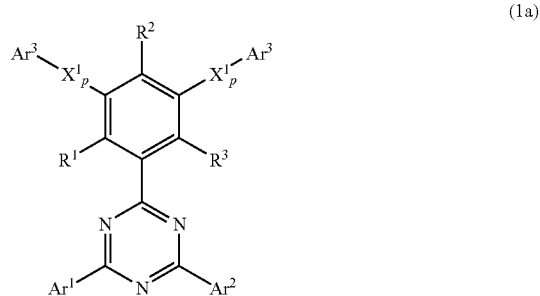

(1a)

wherein Ar$^1$, Ar$^2$, R$^1$, R$^2$, R$^3$, X$^1$, p and Ar$^3$ are the same as defined below with regard to formulae (2a) and (3),
comprising coupling a compound of formula (2a) with a compound of formula (3) in the presence of a metal catalyst;

$$M-X^1_p-Ar^3 \quad (2a)$$

wherein
X$^1$ represents a phenylene group, a naphthylene group or a pyridylene group, wherein these groups may have one or more substituents selected from an alkyl group having 1 to 4 carbon atoms and a fluorine atom;
p represents an integer in the range of 0 to 2, wherein, when p is 2, the adjacent X$^1$s may be the same or different;
Ar$^3$ represents a pyridyl group which may have one or more substituents selected from an alkyl group having 1 to 4 carbon atoms and a fluorine atom, or a phenyl group which may have one or more substituents selected from an alkyl group having 1 to 4 carbon atoms and a fluorine atom; and
M represents a —ZnR$^4$ group, a —MgR$^5$ group, a —SnR$^6$R$^7$R$^8$ group, a —B(OH)$_2$ group, a —BR$^9$ group, a —BF$_3^-$(Z$^1$)$^+$ group or a —SiR$^{10}$R$^{11}$R$^{12}$ group, wherein R$^4$ and R$^5$ represent a chlorine atom, a bromine atom or an iodine atom; R$^6$, R$^7$ and R$^8$ each independently represent an alkyl group having 1 to 4 carbon atoms; R$^9$ represents a methoxy group, an isopropoxy group, a 2,3-dimethylbutane-2,3-dioxy group, an ethylenedioxy group, a 1,3-propanedioxy group or 1,2-phenylenedioxy group; (Z$^1$)$^+$ represents an alkali metal ion or a quaternary ammonium ion; and R$^{10}$, R$^{11}$ and R$^{12}$ each independently represent a methyl group, an ethyl group, a methoxy group, an ethoxy group or a chlorine atom;

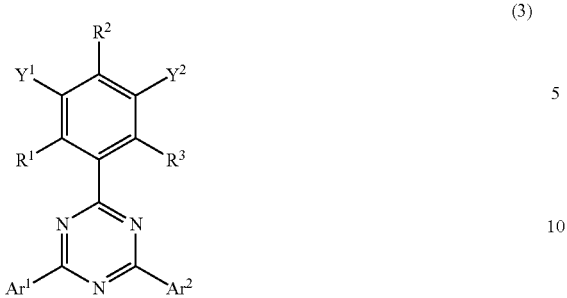

(3)

wherein
- $Ar^1$ and $Ar^e$ each independently represent a phenyl group, a naphthyl group or a biphenylyl group, wherein these groups may have one or more substituents selected from an alkyl group having 1 to 6 carbon atoms and a trifluoromethyl group;
- $R^1$, $R^2$ and $R^3$ each independently represent a hydrogen atom or a methyl group; and
- $Y^1$ and $Y^2$ each independently represent a chorine atom, a bromine atom, an iodine atom or a trifluoromethylsulfonyloxy group.

4. The production process according to claim 3, wherein $Ar^3$ represents a pyridyl group which may have one or more substituents selected from an alkyl group having 1 to 4 carbon atoms and a fluorine atom.

5. A process for producing a phenyl-substituted 1,3,5-triazine compound of formula (1):

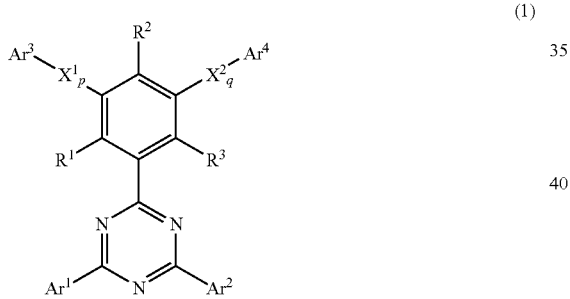

(1)

wherein $Ar^1$, $Ar^2$, $R^1$, $R^2$, $R^3$, $X^1$, $X^2$, p, q, $Ar^3$ and $Ar^4$ are the same as defined below with regard to formulae (2a), (3) and (2b),
comprising coupling a compound of formula (2a) with a compound of formula (3) in the presence of a metal catalyst to give a compound of formula (4); and then, coupling the compound of formula (4) with a compound of formula (2b) in the presence of a metal catalyst;

(2a)

wherein
- $X^1$ represents a phenylene group, a naphthylene group or a pyridylene group, wherein these groups may have one or more substituents selected from an alkyl group having 1 to 4 carbon atoms and a fluorine atom;
- p represents an integer in the range of 0 to 2, wherein, when p is 2, the adjacent $X^1$s may be the same or different;
- $Ar^3$ represents a pyridyl group which may have one or more substituents selected from an alkyl group having 1 to 4 carbon atoms and a fluorine atom, or a phenyl group which may have one or more substituents selected from an alkyl group having 1 to 4 carbon atoms and a fluorine atom; and
- M represents a $-ZnR^4$ group, a $-MgR^5$ group, a $-SnR^6R^7R^8$ group, a $-B(OH)_2$ group, a $-BR^9$ group, a $-BF_3^-(Z^1)^+$ group or a $-SiR^{10}R^{11}R^{12}$ group, wherein $R^4$ and $R^5$ represent a chlorine atom, a bromine atom or an iodine atom; $R^6$, $R^7$ and $R^8$ each independently represent an alkyl group having 1 to 4 carbon atoms; $R^9$ represents a methoxy group, an isopropoxy group, a 2,3-dimethylbutane-2,3-dioxy group, an ethylenedioxy group, a 1,3-propanedioxy group or a 1,2-phenylenedioxy group; $(Z^1)^+$ represents an alkali metal ion or a quaternary ammonium ion; and $R^{10}$, $R^{11}$ and $R^{12}$ each independently represent a methyl group, an ethyl group, a methoxy group, an ethoxy group or a chlorine atom;

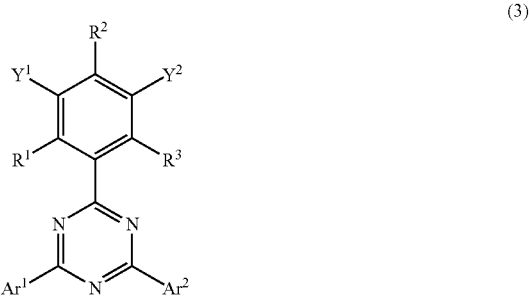

(3)

wherein
- $Ar^1$ and $Ar^2$ each independently represent a phenyl group, a naphthyl group or a biphenylyl group, wherein these groups may have one or more substituents selected from an alkyl group having 1 to 6 carbon atoms and a trifluoromethyl group;
- $R^1$, $R^2$ and $R^3$ each independently represent a hydrogen atom or a methyl group; and
- $Y^1$ and $Y^2$ each independently represent a chorine atom, a bromine atom, an iodine atom or a trifluoromethylsulfonyloxy group;

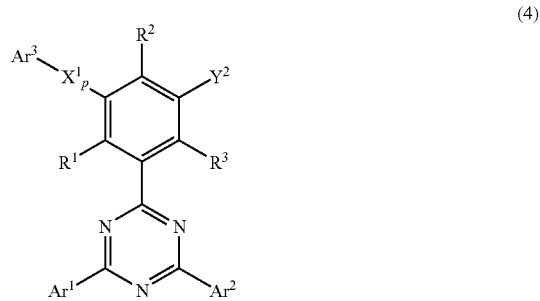

(4)

wherein $Ar^1$, $Ar^2$, $R^1$, $R^2$, $R^3$, $X^1$, p, $Ar^3$ and $Y^2$ are defined above with regard to the formulae (2a) and (3);

(2b)

wherein
- $X^2$ represents a phenylene group, a naphthylene group or pyridylene group, wherein these groups may have one or more substituents selected from an alkyl group having 1 to 4 carbon atoms and a fluorine atom;

q represents an integer in the range of 0 to 2, wherein, when q is 2, the adjacent $X^2$s may be the same or different;

$Ar^4$ represents a pyridyl group which may have one or more substituents selected from an alkyl group having 1 to 4 carbon atoms and a fluorine atom, or a phenyl group which may have one or more substituents selected from an alkyl group having 1 to 4 carbon atoms and a fluorine atom; and M is defined above with regard to formula (2a).

6. The production process according to claim 5, wherein either one or both of $Ar^3$ and $Ar^4$ represents a pyridyl group which may have one or more substituents selected from an alkyl group having 1 to 4 carbon atoms and a fluorine atom.

7. A process for producing a phenyl-substituted 1,3,5-triazine compound of formula (1):

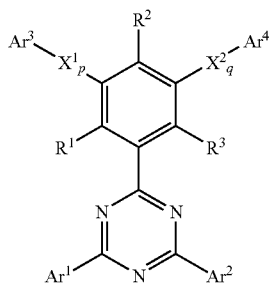

(1)

wherein $Ar^1$, $Ar^2$, $R^1$, $R^2$, $R^3$, $X^1$, $X^2$, p, q, $Ar^3$ and $Ar^4$ are the same as defined below with regard to formulae (2b) and (4), comprising coupling a compound of formula (2b) with a compound of formula (4) in the presence of a metal catalyst;

(2b)

wherein $X^2$ represents a phenylene group, a naphthylene group or a pyridylene group, wherein these groups may have one or more substituents selected from an alkyl group having 1 to 4 carbon atoms and a fluorine atom;

q represents an integer in the range of 0 to 2, wherein, when q is 2, the adjacent $X^2$s may be the same or different;

$Ar^4$ represents a pyridyl group which may have one or more substituents selected from an alkyl group having 1 to 4 carbon atoms and a fluorine atom, or a phenyl group which may have one or more substituents selected from an alkyl group having 1 to 4 carbon atoms and a fluorine atom; and M represents a —$ZnR^4$ group, a —$MgR^5$ group, a —$SnR^6R^7R^8$ group, a —$B(OH)_2$ group, a —$BR^9$ group, a —$BF_3^-(Z^1)^+$ group or a —$SiR^{10}R^{11}R^{12}$ group, wherein $R^4$ and $R^5$ represent a chlorine atom, a bromine atom or an iodine atom; $R^6$, $R^7$ and $R^8$ each independently represent an alkyl group having 1 to 4 carbon atoms; $R^9$ represents a methoxy group, an isopropoxy group, a 2,3-dimethylbutane-2,3-dioxy group, an ethylenedioxy group, a 1,3-propanedioxy group or a 1,2-phenylenedioxy group; $(Z^1)^+$ represents an alkali metal ion or a quaternary ammonium ion; and $R^{10}$, $R^{11}$ and $R^{12}$ each independently represent a methyl group, an ethyl group, a methoxy group, an ethoxy group or a chlorine atom;

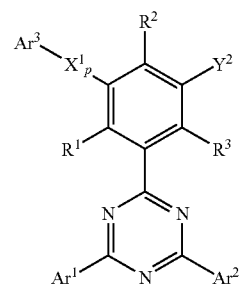

(4)

wherein $Ar^1$ and $Ar^2$ each independently represent a phenyl group, a naphthyl group or a biphenylyl group, wherein these groups may have one or more substituents selected from an alkyl group having 1 to 6 carbon atoms and a trifluoromethyl group;

$R^1$, $R^2$ and $R^3$ each independently represent a hydrogen atom or a methyl group; and $X^1$ represents a phenylene group, a naphthylene group or a pyridylene group, wherein these groups may have one or more substituents selected from an alkyl group having 1 to 4 carbon atoms and a fluorine atom;

p represents an integer in the range of 0 to 2, wherein, when p is 2, the adjacent $X^1$s may be the same or different; and $Ar^3$ represents a pyridyl group which may have one or more substituents selected from an alkyl group having 1 to 4 carbon atoms and a fluorine atom, or a phenyl group which may have one or more substituents selected from an alkyl group having 1 to 4 carbon atoms and a fluorine atom; and $Y^2$ represents a chorine atom, a bromine atom, an iodine atom or a trifluoromethylsulfonyloxy group.

8. The production process according to claim 7, wherein either one or both of $Ar^3$ and $Ar^4$ represents a pyridyl group which may have one or more substituents selected from an alkyl group having 1 to 4 carbon atoms and a fluorine atom.

9. The production process according to claim 3, wherein the metal catalyst is a palladium catalyst, a nickel catalyst or an iron catalyst.

10. The production process according to claim 3, wherein the metal catalyst is a palladium catalyst.

11. The production process according to claim 5, wherein the metal catalyst is a palladium catalyst, a nickel catalyst or an iron catalyst.

12. The production process according to claim 7, wherein the metal catalyst is a palladium catalyst, a nickel catalyst or an iron catalyst.

* * * * *

UNITED STATES PATENT AND TRADEMARK OFFICE
CERTIFICATE OF CORRECTION

PATENT NO. : 8,268,997 B2 Page 1 of 1
APPLICATION NO. : 12/595795
DATED : September 18, 2012
INVENTOR(S) : Tetsu Yamakawa et al.

It is certified that error appears in the above-identified patent and that said Letters Patent is hereby corrected as shown below:

At column 57, line 16 (claim 3, line 15) of the printed patent, please change "$Ar^e$" to --$Ar^2$--.

Signed and Sealed this
Eighth Day of January, 2013

David J. Kappos
*Director of the United States Patent and Trademark Office*